(12) United States Patent
Frenette et al.

(10) Patent No.: US 6,180,650 B1
(45) Date of Patent: Jan. 30, 2001

(54) HETEROSUBSTITUTED PYRIDINE DERIVATIVES AS PDE 4 INHIBITORS

(75) Inventors: Richard Frenette, Laval; Richard Friesen, Kirkland; Mario Girard, St-Lazare; Yves Girard, Ille Bizard; Cedrickx Godbout, Montreal; Daaniel Guay, Ile Perrot; Pierre Hamel, Laval; Helene Perrier, St-Lazare, all of (CA)

(73) Assignee: Merck Frosst Canada & Co., Quebec (CA)

( * ) Notice: Under 35 U.S.C. 154(b), the term of this patent shall be extended for 0 days.

(21) Appl. No.: 09/525,600

(22) Filed: Mar. 14, 2000

Related U.S. Application Data

(60) Provisional application No. 60/130,690, filed on Apr. 23, 1999.

(51) Int. Cl.⁷ .......................... C07D 401/02; A61K 31/44

(52) U.S. Cl. .......................... 514/333; 514/335; 546/256; 546/261

(58) Field of Search .................... 546/256, 261; 514/333, 335

(56) References Cited

FOREIGN PATENT DOCUMENTS

330939 * 2/1989 (EP) ...................................... 514/333

OTHER PUBLICATIONS

Beavo et al, TIPS, vol. 11, pp. 150–150, 1990.*

* cited by examiner

*Primary Examiner*—Zinna Northington Davis
(74) *Attorney, Agent, or Firm*—Shu M. Lee; David L. Rose

(57) ABSTRACT

The invention encompasses the novel compound of Formula I useful in the treatment of diseases, including asthma, by raising the level of cyclic adenosine-3',5'-monophosphate (cAMP) through the inhibition of phosphodiesterase IV (PDE 4).

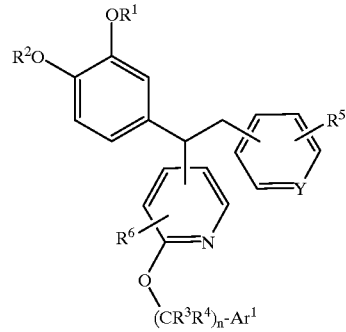

The invention also encompasses pharmaceutical compositions and methods for treatment.

21 Claims, No Drawings

HETEROSUBSTITUTED PYRIDINE DERIVATIVES AS PDE 4 INHIBITORS

This application claims the benefit of priority to Provisional Application No. 60/130,690 filed Apr. 23, 1999.

BACKGROUND OF THE INVENTION

This invention relates to compounds and pharmaceutical compositions containing such compounds useful for treating diseases by raising the level of cyclic adenosine-3',5'-monophosphate (cAMP) through the inhibition of phosphodiesterase IV (PDE 4).

Many hormones and neurotransmitters modulate tissue function by elevating intra-cellular levels of 3',5'-cyclic adenosine monophosphate (cAMP). The cellular levels of cAMP are regulated by mechanisms which control synthesis and breakdown. The synthesis of cAMP is controlled by adenyl cyclase which may be directly activated by agents such as forskolin or indirectly activated by the binding of specific agonists to cell surface receptors which are coupled to adenyl cyclase. The breakdown of cAMP is controlled by a family of phosphodiesterase (PDE) isoenzymes, which also control the breakdown of guanosine 3',5'-cyclic monophosphate (cGMP). To date, nine members of the family have been described (PDE 1-9) the distribution of which varies from tissue to tissue. This suggests that specific inhibitors of PDE isoenzymes could achieve differential elevation of cAMP in different tissues, [for reviews of PDE distribution, structure, function and regulation, see Beavo & Reifsnyder (1990) TIPS, 11: 150–155, Nicholson et al (1991) TIPS, 12: 19–27 and Houslay et al (1998) Adv. Pharmacol. 44: 225–342].

The availability of PDE isotype selective inhibitors has enabled the role of PDEs in a variety of cell types to be investigated. In particular it has been established that PDE 4 controls the breakdown of cAMP in many inflammatory cells, for example, basophils (Peachell P. T. et al., (1992) J. Immunol. 148 2503–2510) and eosinophils (Dent G. et al., (1991) Br. J. Pharmacol. 103 1339–1346) and that inhibition of this isotype is associated with the inhibition of cell activation. Furthermore, elevation of cAMP in airway smooth muscle has a spasmolytic effect. Consequently PDE 4 inhibitors are currently being developed as potential anti-inflammatory drugs particularly for the prophylaxis and treatment of asthma, by achieving both anti-inflammatory and bronchodilator effects.

The application of molecular cloning to the study of PDEs has revealed that for each isotype there may be one or more isoforms. For PDE 4, it is has been shown that there are four isoforms (A, B, C and D) each coded for by a separate gene in both rodents (Swinnen J. V. et al., (1989) Proc. Natl. Acad. Sci. USA 86 5325–5329) and man (Bolger G. et al., (1993) Mol. Cell Biol. 13 6558–6571).

The existence of multiple PDE 4s raises the prospect of obtaining inhibitors that are selective for individual isoforms, thus increasing the specificity of action of such inhibitors. This assumes that the different PDE 4 isoforms are functionally distinct. Indirect evidence in support of this comes from the selective distribution of these isoforms in different tissues (Swinnen et al., 1989; Bolger et al., 1993; Obemolte R. et al., (1993) Gene 129 239–247, ibid) and the high degree of sequence conservation amongst isoforms of different species.

To date full length cDNAs for human PDE 4A, B, C and D (Bolger et al., 1993 ibid; Obernolte et al., 1993 ibid; Mclaughlin M. et al., (1993) J. Biol. Chem. 268 6470–6476, Owens et al (1997) Cell. Signal., 9: 575–585) and rat PDE 4A, B and D (Davis R. et al., (1989) Proc. Natl. Acad. Sci. USA 86 3604–3608; Swinnen J. V. et al., (1991) J. Biol. Chem. 266 18370–18377), have been reported, enabling functional recombinant enzymes to be produced by expression of the cDNAs in an appropriate host cell. These cDNAs have been isolated by conventional hybridisation methods.

The design of PDE 4 inhibitors for the treatment of inflammatory diseases such as asthma, has met with limited success to date. Many of the PDE 4 inhibitors which have been synthesised have lacked potency and/or inhibit more than one type of PDE isoenzyme in a non-selective manner. PDE 4 inhibitors that are relatively potent and selective for PDE 4, are reported to be emetic as well. Indeed this side effect has been so universal that experts have expressed their belief that the emesis experienced upon administration of a PDE 4 inhibitor, may be mechanism based.

One object of the present invention is to provide heterosubstituted pyridines derivatives that are inhibitors of PDE 4 at concentrations at which they have little or no inhibitory action on other PDE isoenzymes. These compounds inhibit the human recombinant PDE 4 enzyme and also elevate cAMP in isolated leukocytes. The compounds thus prevent, alleviate or reduce inflammation in the lungs, such as that induced by carrageenan, platelet-activating factor (PAF), interleukin-5 (IL-5) or antigen challenge. The compounds also suppress the hyperresponsiveness of airway smooth muscle seen in inflammed lungs.

Another object of the present invention is to provide compounds that have good oral activity and that at orally effective doses, exhibit a reduced incidence of the side-effects associated with known PDE 4 inhibitors, such as rolipram. The compounds of the invention are therefore of use in medicine, especially in the prophylaxis and treatment of asthma and other inflammatory conditions.

SUMMARY OF THE INVENTION

A compound represented by formula I:

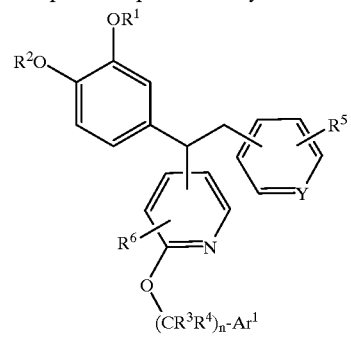

or a pharmaceutically acceptable salt or hydrate thereof wherein:

Y represents N or N-oxide;

$R^1$ and $R^2$ are independently selected from:
H, $C_{1-6}$alkyl and halo$C_{1-6}$ alkyl, $R^3$ and $R^4$ are independently selected from H and $C_{1-6}$alkyl, or $R^3$ and $R^4$ attached to the same carbon atom taken together represent a carbonyl oxygen atom, or $R^3$ and $R^4$ attached to different carbon atoms considered in combination with the carbon atoms to which they are attached along with any intervening atoms and represent a saturated 5, 6 or 7 membered carbocyclic ring, n represents an integer of from 0–6;

$Ar^1$ is selected from the group consisting of:
(a) thienyl,
(b) thiazolyl, (c) pyridyl,
(d) phenyl and
(e) naphthyl,
said $Ar^1$ being optionally substituted with 1–3 members selected from the group consisting of:
(1) halo,
(2) $C_{1-6}$alkoxy,
(3) $C_{1-7}$alkylthio,
(4) CN,
(5) $C_{1-6}$alkyl,
(6) $C_{1-6}$hydroxyalkyl,
(7) —$CO_2H$, —$CO_2C_{1-6}$alkyl,
(8) $NH(SO_2Me)$, $N(SO_2Me)_2$,
(9) $SO_2Me$,
(10) $NO_2$,
(11) $C_{1-6}$alkenyl,
(12) halo $C_{1-6}$ alkyl, and
(13) $NH_2$,
and when $Ar^1$ represents a phenyl or naphthyl group with two or three substituents, two such substituents may be considered in combination and represent a 5 or 6 membered fused lactone ring.

Pharmaceutical compositions and methods of treatment are also included.

DETAILED DESCRIPTION OF THE INVENTION

The present invention includes compounds represented by formula I:

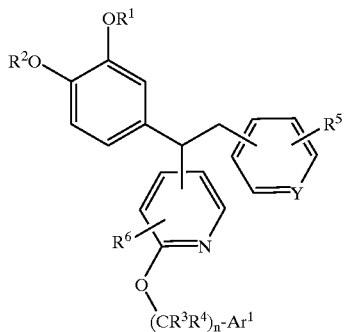

as well as pharmaceutically acceptable salts or hydrate thereof wherein:
Y represents N or N-oxide;
$R^1$ and $R^2$ are independently selected from:
  H, $C_{1-6}$alkyl and halo$C_{1-6}$ alkyl,
$R^3$ and $R^4$ are independently selected from H and $C_{1-6}$alkyl, or $R^3$ and $R^4$ attached to the same carbon atom taken together represent a carbonyl oxygen atom, or
  $R^3$ and $R^4$ attached to different carbon atoms considered in combination with the carbon atoms to which they are attached along with any intervening atoms and represent a saturated 5, 6 or 7 membered carbocyclic ring,
n represents an integer of from 0–6;
$Ar^1$ is selected from the group consisting of:
(a) thienyl,
(b) thiazolyl,
(c) pyridyl,
(d) phenyl and
(e) naphthyl,
said $Ar^1$ being optionally substituted with 1–3 members selected from the group consisting of:
(1) halo,
(2) $C_{1-6}$alkoxy,
(3) $C_{1-7}$alkylthio,
(4) CN,
(5) $C_{1-6}$alkyl,
(6) $C_{1-6}$hydroxyalkyl,
(7) —$CO_2H$, —$CO_2C_{1-6}$alkyl,
(8) $NH(SO_2Me)$, $N(SO_2Me)_2$,
(9) $SO_2Me$,
(10) $NO_2$,
(11) $C_{1-6}$alkenyl,
(12) halo $C_{1-6}$ alkyl, and
(13) $NH_2$,
and when $Ar^1$ represents a phenyl or naphthyl group with two or three substituents, two such substituents may be considered in combination and represent a 5 or 6 membered fused lactone ring.

The following definitions pertain to the terms used herein unless otherwise indicated.

Halo is intended to include F, Cl, Br, and I. Halo$C_{1-6}$ alkyl refers to an alkyl group having 1–9 halo groups attached. Examples include —$CH_2F$, —$CHF_2$, —$CF_3$, —$CH_2CH_2F$, —$CHFCH_2F$, —$CF_2CH_2F$, —$CF_2CHF_2$ and —$CF_2CF_3$.

Alkyl groups include straight or branched alkyl groups having 1–7 carbon atoms, and cyclic alkyl groups having from 3–7 carbon atoms. Cycloalkyl groups with alkyl substituent groups attached are also included. Examples of $C_{1-6}$alkyl groups include methyl, ethyl, propyl, 2-propyl, s- and t-butyl, butyl, pentyl, hexyl, 1,1-dimethylethyl, cyclopropyl, cyclobutyl, cyclopentyl and cyclohexyl. Examples of $C_{1-6}$alkoxy groups include methoxy, ethoxy, propoxy, isopropoxy, cyclopropyloxy, cyclohexyloxy, and the like.

Likewise, $C_{1-7}$alkylthio is intended to include alkylthio groups of from 1 to 7 carbon atoms of a straight, branched or cyclic configuration. Examples of alkylthio groups include methylthio, propylthio, isopropylthio, cycloheptylthio, etc. By way of illustration, the propylthio group signifies —$SCH_2CH_2CH_3$.

Preferred values of $R^1$ and $R^2$ are $C_{1-6}$ alkyl and halo$C_{1-6}$alkyl. More preferred values are selected from the group consisting of $CH_3$, $CH_2F$, $CHF_2$, $CF_3$ and most preferably $CHF_2$. Within this subset, all other variables are as originally defined.

Preferred values of n are 0, 1, 2 and 3. More preferred values are 0, 1 and 2. Within these subsets, all other variables are as originally defined.

Preferred values of $Ar^1$ are phenyl and naphthyl. More preferred is phenyl. Within these subsets, all other variables are as originally defined.

Preferred values of $R^3$ and $R^4$ are H and $C_{1-6}$alkyl. More preferred are H and methyl. Within these subsets, all other variables are as originally defined.

Preferred values of $R^5$ and $R^6$ are H and $C_{1-6}$alkyl. More preferred is H. Within these subsets, all other variables are as originally defined.

Preferably the Y is in the 2, 3 or 4 position relative to the point of attachment to the ethylene group. More preferably the Y is in the 4 position relative to the point of attachment to the ethylene group.

Similarly, the pyridyl nitrogen atom shown is preferably in the 2, 3 or 4 position, relative to the attachment to the ethylene group. More preferably it is in the 3 position.

A subset of compounds that is of particular interest relates to compounds of formula I wherein:
  $R^1$ and $R^2$ are $C_{1-6}$alkyl and halo$C_{1-6}$alkyl selected from the group consisting of $CH_3$, $CH_2F$, $CHF_2$ and $CF_3$;
  n is 0, 1, 2 or 3;

Ar$^1$ is phenyl or naphthyl;

R$^3$ and R$^4$ are H and methyl and

R$^5$ and R$^6$ are H or C$_{1-6}$alkyl.

Within this subset, all other variables are as originally defined.

More particularly, a subset of compounds that is of particular interest relates to compounds of formula I wherein:

R$^1$ and R$^2$ are CHF$_2$, and n is 0, 1 or 2. Within this subset, all other variables are as defined immediately above.

Another subset of compounds that is of particular interest relates to compounds of formula I wherein:

R$^1$ and R$^2$ are CHF$_2$;

n is 0, 1 or 2;

R$^3$ and R$^4$ are H or methyl, R$^5$ and R$^6$ are H and

Ar$^1$ is phenyl.

Within this subset, all other variables are as defined immediately above.

Examples of compounds falling within the present invention include the following:

1. 4-{2-[3,4-Bis(difluoromethoxy)phenyl]-2-{6-[4-(trifluoromethoxy)phenoxy]3-pyridyl}ethyl}pyridine-N-oxide,
2. 4-{2-[3,4-Bis(difluoromethoxy)phenyl]-2-[6-(4-(methoxycarbonyl)phenoxy)3-pyridyl]ethyl}pyridine,
3. 4-{2-[3,4-Bis(difluoromethoxy)phenyl]-2-[6-(4-(methoxycarbonyl)phenoxy)3-pyridyl]ethyl}pyridine-N-oxide,
4. 4-{2-[3,4-Bis(difluoromethoxy)phenyl]-2-{6-[4-(2-hydroxypropan-2-yl)phenoxy]3-pyridyl}ethyl}pyridine,
5. 4-{2-[3,4-Bis(difluoromethoxy)phenyl]-2-{6-[4-(2-hydroxypropan-2-yl)phenoxy]3-pyridyl}ethyl}pyridine-N-oxide,
6. 4-{2-[3,4-Bis(difluoromethoxy)phenyl]-2-[6-(4-nitrophenoxy)3-pyridyl]ethyl}pyridine-N-oxide,
7. 4-{2-[3,4-Bis(difluoromethoxy)phenyl]-2-{6-[4-(methylsulfonylamino)phenoxy]3-pyridyl}ethyl}pyridine-N-oxide,
8. 4-{2-[3,4-Bis(difluoromethoxy)phenyl]-2-{6-[4-(trifluoromethyl)phenoxy]3-pyridyl}ethyl}pyridine-N-oxide,
9. 4-{2-[3,4-Bis(difluoromethoxy)phenyl]-2-{6-[3-(methylsulfonylamino)phenoxy]3-pyridyl}ethyl}pyridine-N-oxide,
10. 4-{2-[3,4-Bis(difluoromethoxy)phenyl]-2-{6-[4-(2-propenyl)phenoxy]3-pyridyl}ethyl}pyridine-N-oxide,
11. 4-{2-[3,4-Bis(difluoromethoxy)phenyl]-2-{6-[4-(2-propyl)phenoxy]3-pyridyl}ethyl}pyridine-N-oxide,
12. 4-{2-[3,4-Bis(difluoromethoxy)phenyl]-2-{6-[4-(dimethylsulfonylamino)phenoxy]3-pyridyl}ethyl}pyridine-N-oxide,
13. 4-{2-[3,4-Bis(difluoromethoxy)phenyl]-2-{6-[(4-hydroxymethyl-3-arboxyl)phenoxy]3-pyridyl}ethyl}pyridine-N-oxide sodium salt,
14. 4-{2-[3,4-Bis(difluoromethoxy)phenyl]-2-[6-(benzyloxy)3-pyridyl]ethyl}pyridine-N-oxide,
15. 4-{2-[3,4-Bis(difluoromethoxy)phenyl]-2-[6-(1-phenylethoxy)3-pyridyl]ethyl}pyridine-N-oxide,
16. 4-{2-[3,4-Bis(difluoromethoxy)phenyl]-2-[6-(3,4-difluorobenzyloxy)3-pyridyl]ethyl}pyridine-N-oxide,
17. 4-{2-[3,4-Bis(difluoromethoxy)phenyl]-2-[6-(4-methylsulfonylbenzyloxy)3-pynrdyl]ethyl}pyridine-N-oxide,
18. (Enantiomer-1)-4-{2-[3,4-Bis(difluoromethoxy)phenyl]-2-[6-(3,5-difluorobenzyloxy)3-pyridyl]ethyl}pyridine,
19. (Enantiomer-2)-4-{2-[3,4-Bis(difluoromethoxy)phenyl]-2-[6-(3,5-difluorobenzyloxy)3-pyridyl]ethyl}pyridine,
20. (Enantiomer-1)-4-{2-[3,4-Bis(difluoromethoxy)phenyl]-2-[6-(3,5-difluorobenzyloxy)3-pyridyl]ethyl}pyridine-N-oxide,
21. (Enantiomer-2)-4-{2-[3,4-Bis(difluoromethoxy)phenyl]-2-[6-(3,5-difluorobenzyloxy)3-pyridyl]ethyl}pyridine-N-oxide,
22. 4-{2-[3,4-Bis(difluoromethoxy)phenyl]-2-{6-[2-methyl-2-(4-fluorophenyl)propyloxy]3-pyridyl}ethyl}pyridine,
23. 4-{2-[3,4-Bis(difluoromethoxy)phenyl]-2-{6-[2-methyl-2-(4-fluorophenyl)propyloxy]3-pyridyl}ethyl}pyridine-N-oxide,
24. 4-{2-[3,4-Bis(difluoromethoxy)phenyl]-2-{6-[2-(4-fluorophenyl)ethoxy]3-pyridyl}ethyl}pyridine,
25. 4-{2-[3,4-Bis(difluoromethoxy)phenyl]-2-{6-[2-(4-fluorophenyl)ethoxy]3-pyridyl}ethyl}pyridine-N-oxide,
26. 4-{2-[3,4-Bis(difluoromethoxy)phenyl]-2-[6-(4-trifluoromethylbenzyloxy)3-pyridyl]ethyl}pyridine-N-oxide,
27. 4-{2-[3,4-Bis(difluoromethoxy)phenyl]-2-[6-(4-trifluoromethoxybenzyloxy)3-pyridyl]ethyl}pyridine-N-oxide,
28. 4-{2-[3,4-Bis(difluoromethoxy)phenyl]-2-[6-(1,1-dimethyl-2-phenylethoxy)3-pyridyl]ethyl}pyridine-N-oxide,
29. 4-{2-[3,4-Bis(difluoromethoxy)phenyl]-2-[6-(2-thienylmethoxy)3-pyridyl]ethyl}pyridine-N-oxide,
30. 4-{2-[3,4-Bis(difluoromethoxy)phenyl]-2-{6-[1-methyl-1-(4-fluorophenyl)ethoxy]3-pyridyl}ethyl}pyridine,
31. 4-{2-[3,4-Bis(difluoromethoxy)phenyl]-2-{6-[1-methyl-1-(4-fluorophenyl)ethoxy]3-pyridyl}ethyl}pyridine-N-oxide,
32. 4-{2-[3,4-Bis(difluoromethoxy)phenyl]-2-[6-(4-fluorobenzyloxy)3-pyridyl]ethyl}pyridine-N-oxide,
33. 4-{2-[3,4-Bis(difluoromethoxy)phenyl]-2-[6-(4-chlorobenzyloxy)3-pyridyl]ethyl}pyridine-N-oxide,
34. 4-{2-[3,4-Bis(difluoromethoxy)phenyl]-2-{6-[1,2-dihydro-1-isobenzofuranone-6-oxy]3-pyridyl}ethyl}pyridine-N-oxide.

As used herein, the terms "Enantiomer-1" and "Enamtiomer-2" refer respectively to the fast eluting isomer and the slow eluting isomer when purified by HPLC.

The compounds described herein contain one or more asymmetric centers and may thus give rise to diastereomers and optical isomers. The present invention is meant to include all such possible isomers and diastereomers as well as their racemic and resolved, enantiomerically pure forms and pharmaceutically acceptable salts thereof.

The invention also encompasses a pharmaceutical composition that is comprised of a compound of formula I in combination with a pharmaceutically acceptable carrier.

Preferably the composition is comprised of a pharmaceutically acceptable carrier and a non-toxic therapeutically effective amount of compound of formula I as described above.

Moreover, within this preferred embodiment, the invention encompasses a pharmaceutical composition for the treatment or prevention of disease by inhibition of PDE 4, resulting in an elevation of cAMP, comprising a pharmaceutically acceptable carrier and a non-toxic therapeutically effective amount of compound of formula I as described above.

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, NN-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

It will be understood that references to the compounds of Formula I are meant to also include the pharmaceutically acceptable salts.

The compounds of formula I are selective and potent inhibitors of PDE 4. The biological activity and utility of the compounds may be demonstrated as described herein.

The compounds according to the invention are thus of particular use in the prophylaxis and treatment of human diseases where an unwanted inflammatory response or muscular spasm (for example bladder or alimentary smooth muscle spasm) is present and where elevation of the cAMP levels may be expected to prevent or alleviate the disease or condition.

Particular uses to which the compounds of the invention may be put include the prophylaxis and treatment of asthma, especially inflamed lung associated with asthma, cystic fibrosis, in the treatment of inflammatory airway disease, chronic bronchitis, eosinophilic granuloma, psoriasis and other benign and malignant proliferative skin diseases, endotoxic shock, septic shock, ulcerative colitis, Crohn's disease, reperfusion injury of the myocardium and brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis and atherosclerosis.

The compounds of the invention also suppress neurogenic inflammation. They are, therefore, analgesic, antitussive and antihyperalgesic in inflammatory diseases associated with irritation and pain.

The compounds also elevate cAMP in lymphocytes and thereby suppress unwanted lymphocyte activation in immune-based diseases such as rheumatoid arthritis, ankylosing spondylitis, transplant rejection and graft versus host disease.

The compounds also reduce gastric acid secretion and therefore can be used to treat conditions associated with hypersecretion of gastric acid.

The compounds also suppress cytokine synthesis by inflammatory cells in response to immune or infectious stimulation. They are, therefore, useful in the treatment of bacterial, fungal or viral induced sepsis and septic shock in which cytokines such as tumour necrosis factor (TNF) are key mediators.

The compounds of the invention also suppress inflammation and pyrexia due to cytokines and are, therefore, useful in the treatment of inflammation and cytokine-mediated chronic tissue degeneration which occurs in diseases such as rheumatoid or osteo-arthritis.

The over-production of cytokines such as TNF in bacterial, fungal or viral infections or in diseases such as cancer, leads to cachexia and muscle wasting. Compounds of the invention ameliorate these symptoms as well.

The compounds of the invention elevate cAMP in certain areas of the brain and thereby counteract depression and memory impairment.

Compounds of the invention suppress cell proliferation in certain tumour cells and can be used, therefore, to prevent tumour growth and invasion of normal tissues.

For the prophylaxis or treatment of disease the compounds may be administered as pharmaceutical compositions, and according to a further aspect of the invention we provide a pharmaceutical composition which comprises a compound of formula (1) together with one or more pharmaceutically acceptable carriers, excipients or diluents.

For the treatment or prevention of any of the diseases or conditions described herein, the compounds of formula I may be administered orally, topically, parenterally, by inhalation spray or rectally in formulations containing conventional non-toxic pharmaceutically acceptable carriers, adjuvants and vehicles.

The term parenteral as used herein includes subcutaneous, intradermal, intravenous, intramuscular and intrasternal injection or infusion techniques. In addition to the treatment of warm-blooded animals such as mice, rats, horses, cattle sheep, dogs, cats, etc., the compounds of the invention are useful for the treatment of humans.

Oral pharmaceutical compositions containing the active ingredient are typically in the form of tablets, troches, lozenges, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

In hard gelatin capsules, the active ingredient is typically mixed with an inert solid diluent, for example, calcium carbonate, calcium phosphate or kaolin. In soft gelatin capsules, the active ingredient is typically mixed with water or an oil medium, for example peanut oil, liquid paraffin or olive oil.

Aqueous suspensions contain the active material in admixture with excipients suitable for the manufacture of aqueous suspensions. Such excipients are suspending agents, for example sodium carboxymethyl-cellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsion. The oil phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above.

The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution.

In addition, sterile, fixed oils may be employed as a solvent or suspending medium. For this purpose any bland fixed oil may be employed including synthetic mono- or diglycerides.

In addition, fatty acids such as oleic acid find use in the preparation of injectables.

Compounds of formula I may also be administered in the form of suppositories for rectal administration of the drug. These compositions can be prepared by mixing the drug with a suitable non-irritating excipient which is solid at ordinary temperatures but liquid at normal body temperature and will therefore melt to release the drug. Examples of such materials include cocoa butter and polyethylene glycols.

For topical use, creams, ointments, jellies, solutions or suspensions, containing the compound of Formula I are employed. (For purposes of this application, topical application also includes mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, inflammation may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 500 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the invention can be synthesized using the general synthesis schemes provided below. It will be apparent to one skilled in the art that similar methodology could be used to prepare the enantiomers or the racemates of the illustrated compounds.

The following abbreviations have the indicated meanings:

| | | |
|---|---|---|
| Ac | = | acetyl |
| Bn | = | benzyl |
| cAMP | | cyclic adenosine-3',5'-monophosphate |
| DBU | = | 1,8-diazabicyclo[5.4.0]undec-7-ene |
| DIBAL | = | diisobutylaluminum hydride |
| DMAP | = | 4-(dimethylamino)pyridine |
| DMF | = | N,N-dimethylformamide |
| $Et_3N$ | = | triethylamine |
| GST | | glutathione transferase |
| HMDS | | hexamethyldisilazide |
| LDA | = | lithium diisopropylamide |
| m-CPBA | = | metachloroperbenzoic acid |
| MMPP | = | monoperoxyphthalic acid |
| MPPM | = | monoperoxyphthalic acid, magnesium salt $6H_2O$ |
| Ms | = | methanesulfonyl = mesyl = $SO_2Me$ |
| MsO | = | methanesulfonate = mesylate |
| NSAID | = | non-steroidal anti-inflammatory drug |
| o-Tol | = | ortho-tolyl |
| OXONE® | = | $2KHSO_5 \cdot KHSO_4 \cdot K_2SO_4$ |
| PCC | | pyridinium chlorochromate |
| PDC | = | pyridinium dichromate |
| PDE | | phosphodiesterase |
| Ph | = | phenyl |
| Phe | = | benzenediyl |
| PMB | = | para-methoxybenzyl |
| Pye | = | pyridinediyl |
| r.t. | = | room temperature |
| rac. | | racemic |
| SAM | = | aminosulfonyl or sulfonamide or $SO_2NH_2$ |
| SEM | = | 2-(trimethylsilyl)ethoxymethoxy |
| SPA | = | scintillation proximity assay |
| TBAF | = | tetra-n-butylammonium fluoride |
| Th | = | 2- or 3-thienyl |
| TFA | = | trifluoroacetic acid |
| TFAA | = | trifluoroacetic acid anhydride |
| THF | = | tetrahydrofuran |
| Thi | = | thiophenediyl |
| TLC | | thin layer chromatography |
| TMS-CN | = | trimethylsilyl cyanide |
| TMSI | | trimethylsilyl iodide |
| Tz | = | 1H (or 2H)-tetrazol-5-yl |

| | | |
|---|---|---|
| C₃H₅ | = | allyl |
| Me | = | methyl |
| Et | = | ethyl |
| n-Pr | = | normal propyl |
| i-Pr | = | isopropyl |
| n-Bu | = | normal butyl |
| i-Bu | = | isobutyl |
| s-Bu | = | secondary butyl |
| t-Bu | = | tertiary butyl |
| c-Pr | = | cyclopropyl |
| c-Bu | = | cyclobutyl |
| c-Pen | = | cyclopentyl |
| c-Hex | = | cyclohexyl |

SCHEME 1

The preparation of bromopyridine intermediate 1 is shown in Scheme 1. Monolithiation of 2,5-dibromopyridine followed by the addition 3,4-bis(difluoromethoxy)benzaldehyde as found in U.S. Pat. No. 5,710,170 gave the secondary alcohol which was subsequently oxidized to the corresponding ketone with an oxidizing agent such as $MnO_2$.

SCHEME 1

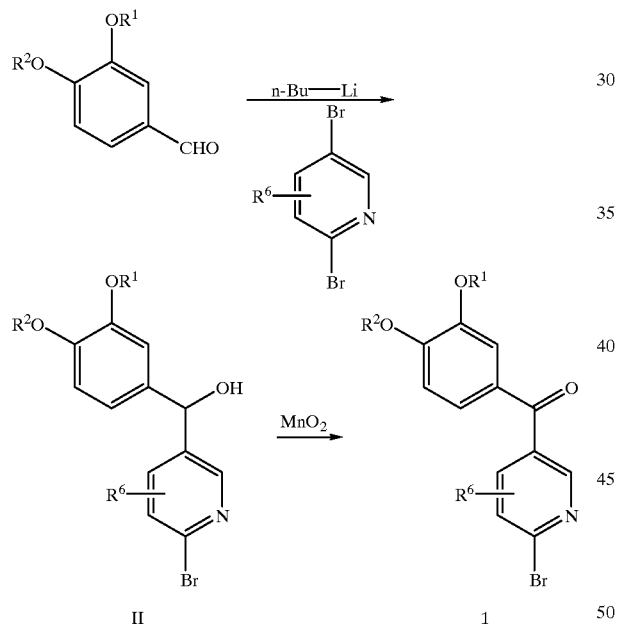

SCHEME 2

The preparation of bromopyridine intermediate 2 and 3 is shown in Scheme 2. The secondary alcohol II was converted to the corresponding chloride III using a chlorinating agent such as thionyl chloride in the presence of a base. This chloride was condensed with the α-anion of ethyl 4-pyridyl acetate, affording the ester IV which upon hydrolysis with a base such as lithium hydroxide, followed by acidification with an acid such as hydrochloric acid afforded the decarboxylated intermediate 2. Oxidation of the pyridine to the pyridine-N-oxide 3 was done with an oxidizing agent such as MMPP.

SCHEME 2

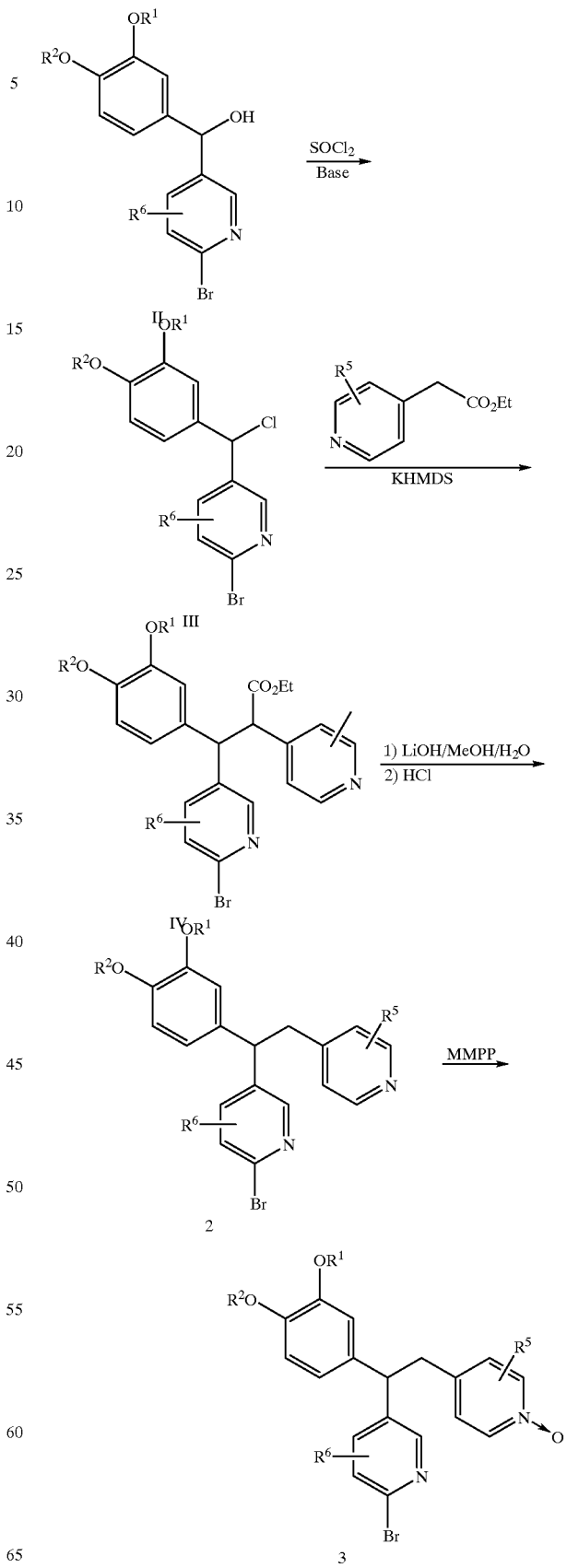

SCHEME 3

The general method for the preparation of substituted alcohols is presented in Scheme 3. Esterification of a suitable carboxylic acid V under Fisher's conditions followed by dialkylation of the methyl ester VI with a base such as LHMDS and a suitable alkylating agent, afforded the corresponding gem-α,α-disubstituted ester VII. This intermediate is converted to the alcohol VIII by reduction with a reducing agent such as lithium aluminum hydride.

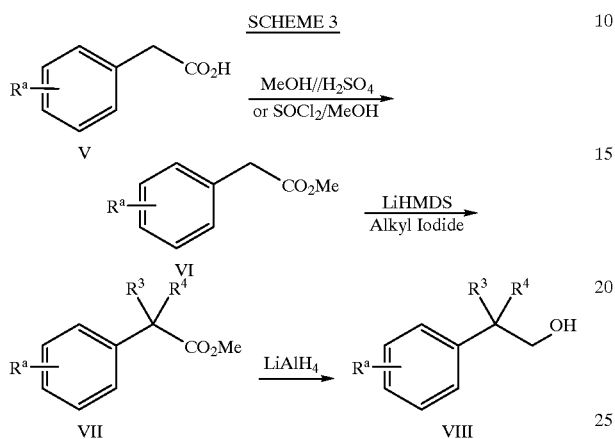

$R^a$ represents a substituent group attached to $Ar^1$, wherein $Ar^1$ represents phenyl. Up to 3 $R^a$ groups may be present. The alkyl iodide provides the source for $R^3$ and $R^4$, which can be the same or different.

SCHEME 4

6-Oxy-3-pyridyl derivatives of formula Ia and Ib were prepared by the general method shown in Scheme 8. Bromopyridine 1 was coupled with a suitable alcohol in the presence of a base such as potassium tert-butoxide. The reduction of the ketone XXI was performed with a reducing agent such as sodium borohydride, followed by the conversion of the corresponding alcohol XXII to the chloride XXII with a chlorinating agent such as thionyl chloride and a suitable base. This chloride was condensed with the α-anion of ethyl 4-pyridyl acetate, affording the ester XXIV which upon hydrolysis with a base such as lithium hydroxide, followed by acidification afforded the decarboxylated intermediate Ia. Oxidation of the pyridine to the pyridine-N-oxide Ib was done with an oxidizing agent such as MMPP. As noted above with respect to scheme 3, $R^a$ represents a substituent group attached to Arn and up to 3 $R^a$ groups may be present.

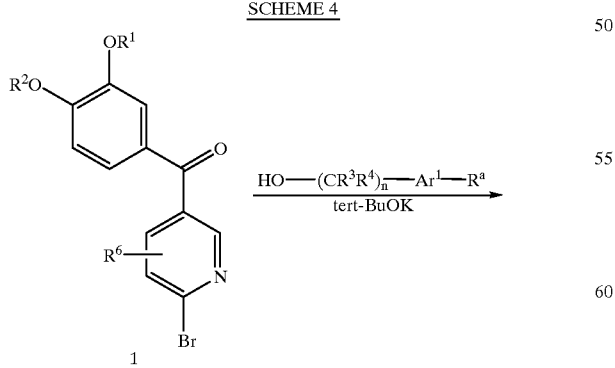

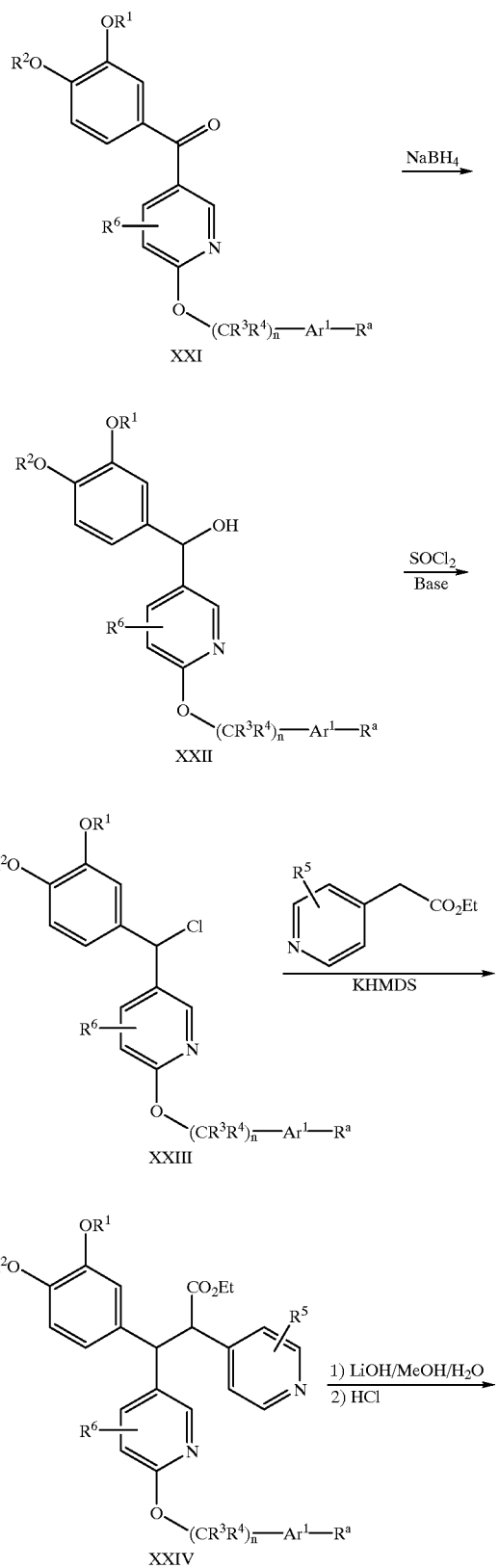

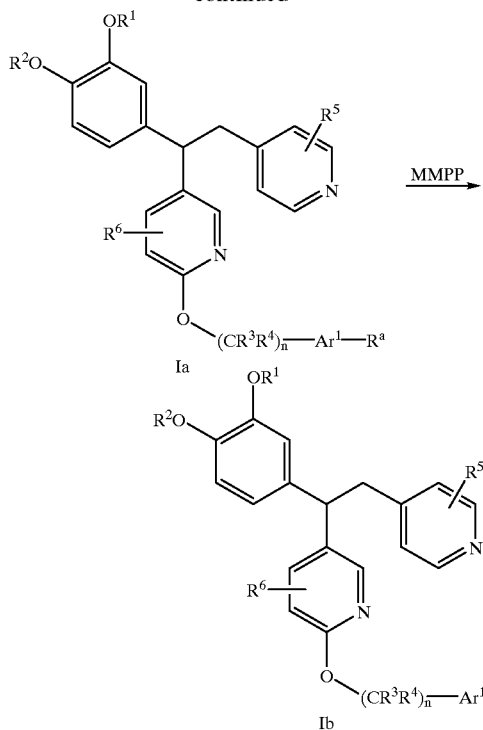

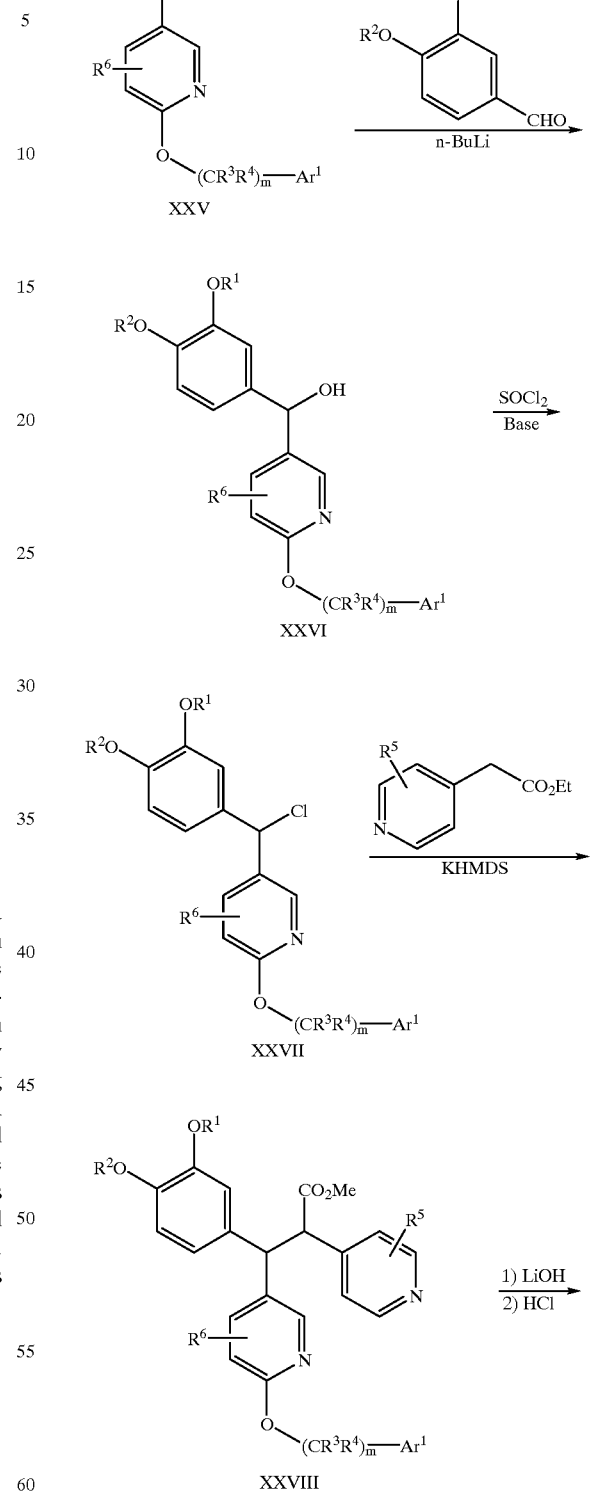

SCHEME 5

Alternatively, 6-Oxy-3-pyridyl derivatives of formula Ia and Ib were prepared by the general method shown in Scheme 9. 2,5-Dibromopyridine was coupled with a suitable alcohol in the presence of a base such as potassium hydroxide. Lithiation of the bromide XXV and condensation with 3,4-bis(substituted) benzaldehyde afforded the secondary alcohol XXVI which was converted to the corresponding chloride XXVII with a chlorinating agent such as thionyl chloride and a suitable base. This chloride was condensed with the α-anion of ethyl 4-pyridyl acetate, affording the ester XXVIII which upon hydrolysis with a base such as lithium hydroxide, followed by acidification with an acid such as HCl afforded the decarboxylated intermediate Ic. Oxidation of the pyridine to the pyridine-N-oxide Id was done with an oxidizing agent such as MMPP.

SCHEME 5

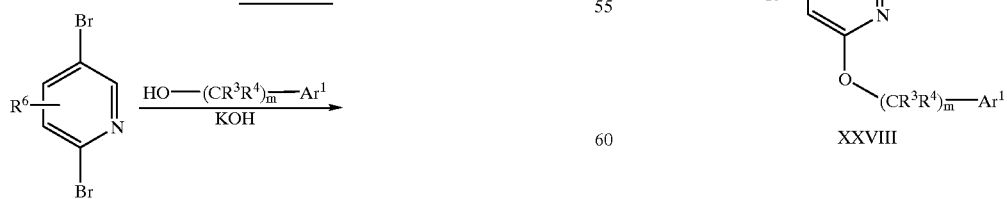

SCHEME 6

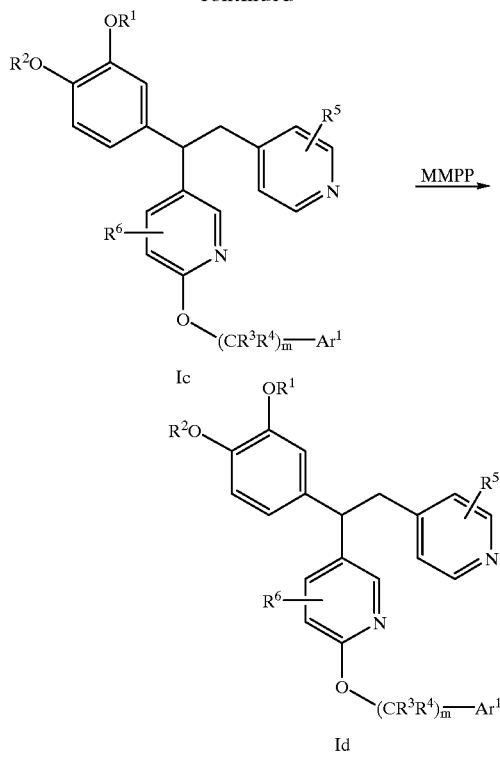

Scheme 6 describes the preparation of several derivatives from the same carboxylic acid $Ia_1$. Treatment of this acid with a methylating agent such as diazomethane afforded the corresponding ester $Ia_2$ which was derivatised to the pyridine-N-oxide $Ib_1$ in the presence of an oxidizing agent such as MMPP and to the tertiary alcohol $Ia_3$ by the addition of an organocerium reagent, such as generated by the reaction of MeMgBr and $CeCl_3$. This tertiary alcohol $Ia_3$ could then by oxidized to the corresponding pyridine-N-oxide $Ib_2$ which upon treatment with an acid such as p-toluenesulfonic acid afforded insaturated derivative $Ib_3$.

SCHEME 6

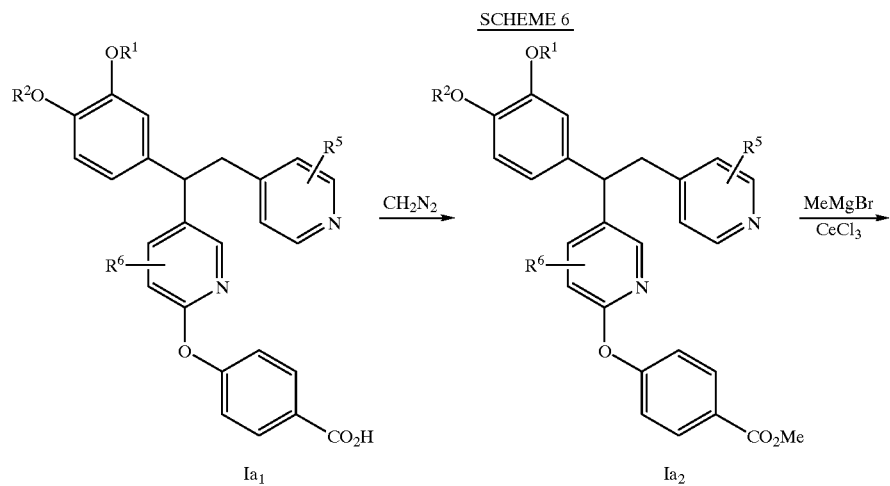

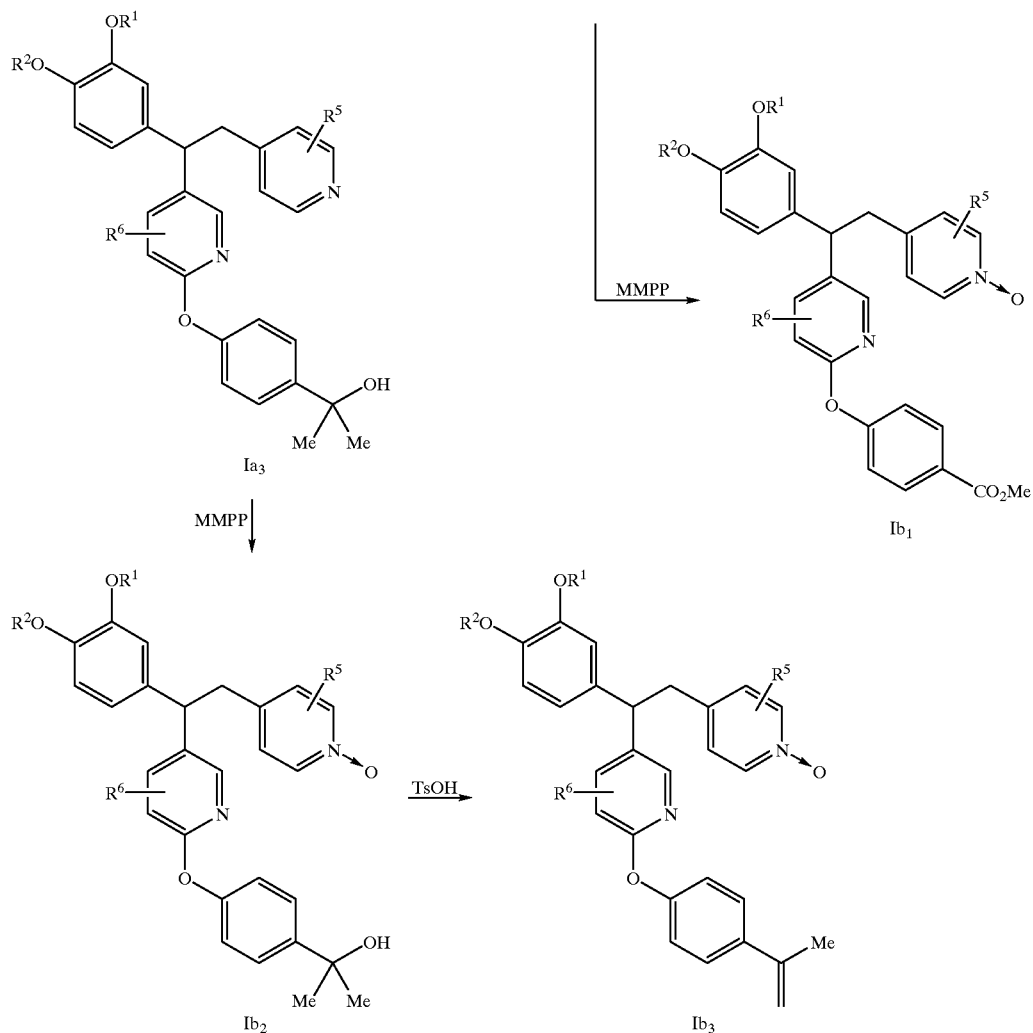

SCHEME 7

Mono and bis(methylsulfonamides) were prepared by the general method presented in Scheme 7. The nitroaryl derivative $Ia_4$ was provided according to Scheme 4. The pyridine bis-sulfonamide $Ia_6$ was obtained by reduction of the nitro group with a reducing agent such as Pd/C under an hydrogen atmosphere followed by sulfonylation of the corresponding amine $Ia_5$ in the presence of a sulfonylating agent such as methylsulfonyl chloride and a suitable base. This common intermediate could then be oxidized to the corresponding pyridine-N-oxide $Ib_4$ with an oxidizing agent such as MMPP or hydrolyzed under basic conditions to the mono-sulfonamide $Ia_7$ followed by the oxidation to the pyridine-N-oxide with an oxidizing agent such as MMPP.

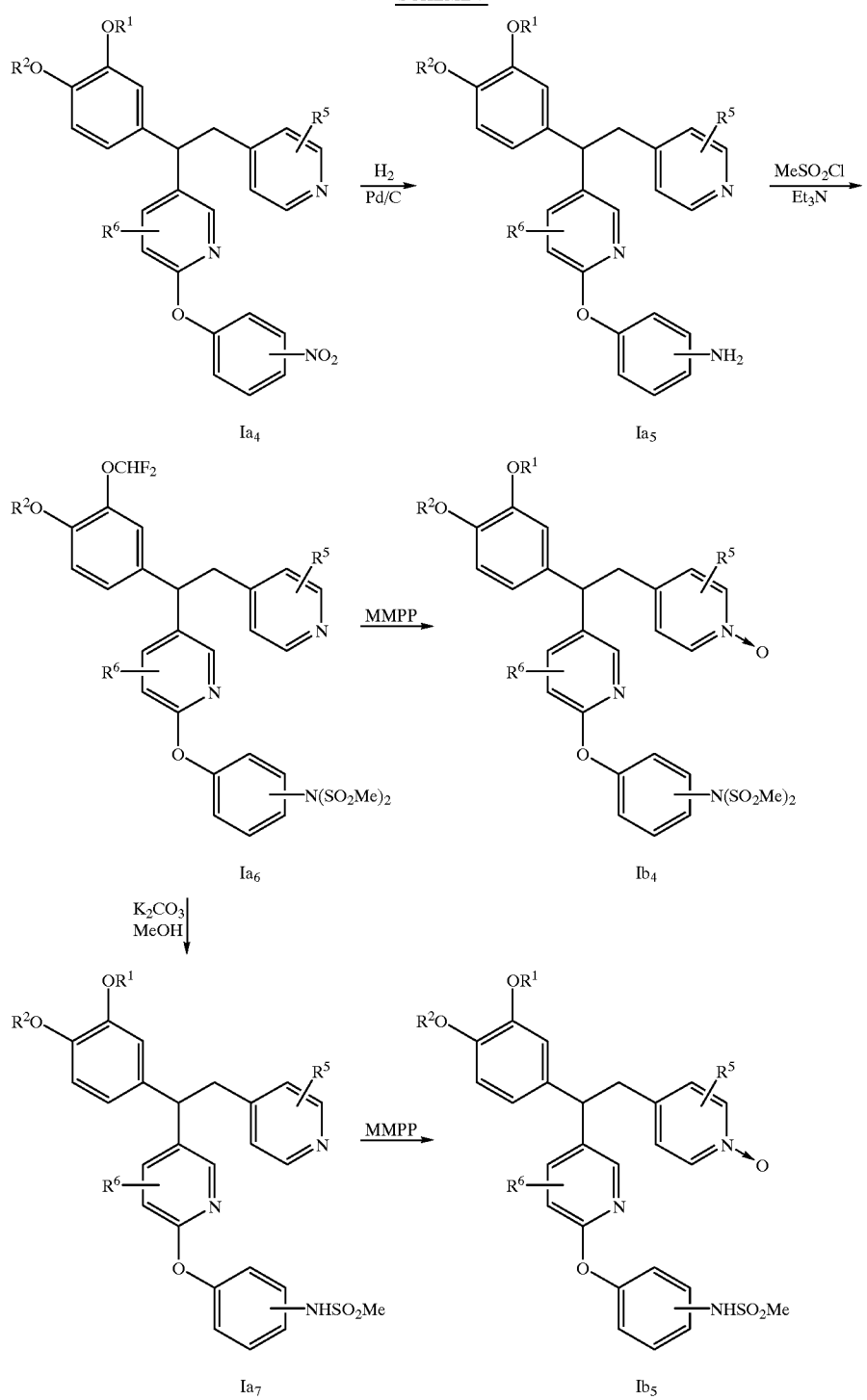

SCHEME 8

Methylsulfone $Ib_6$ was prepared by the method presented in Scheme 8. Thioether XXIIa was oxidized to the sulfone in the presence of an oxidizing agent such as MMPP followed by the conversion of the secondary alcohol to the corresponding chloride with a chlorination agent such as thionyl chloride and a base such as Hunig's base. This chloride XXIIIa was condensed with the α-anion of ethyl 4-pyridyl acetate, affording the ester XXIVa which upon hydrolysis with a base such as lithium hydroxide, followed by acidification with an acid such as hydrochloric acid afforded the decarboxylated intermediate. Oxidation of the pyridine to the pyridine-N-oxide $Ib_6$ was done with an oxidizing agent such as MMPP.

SCHEME 8
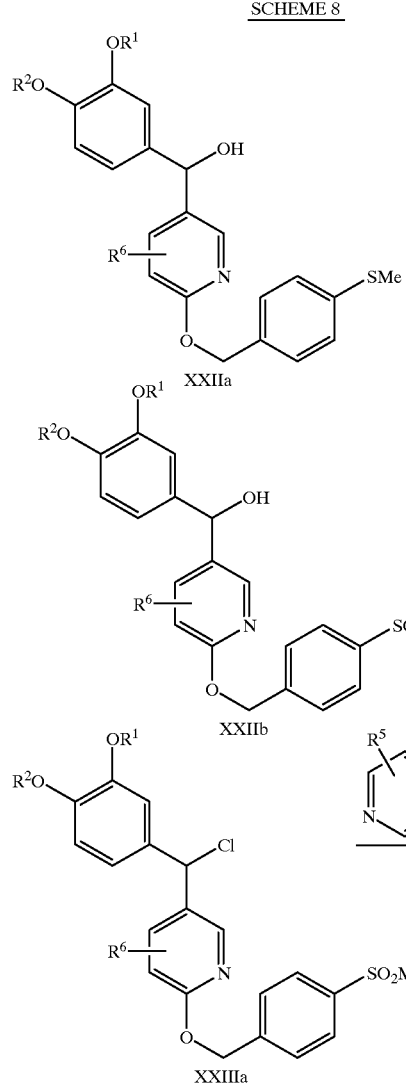
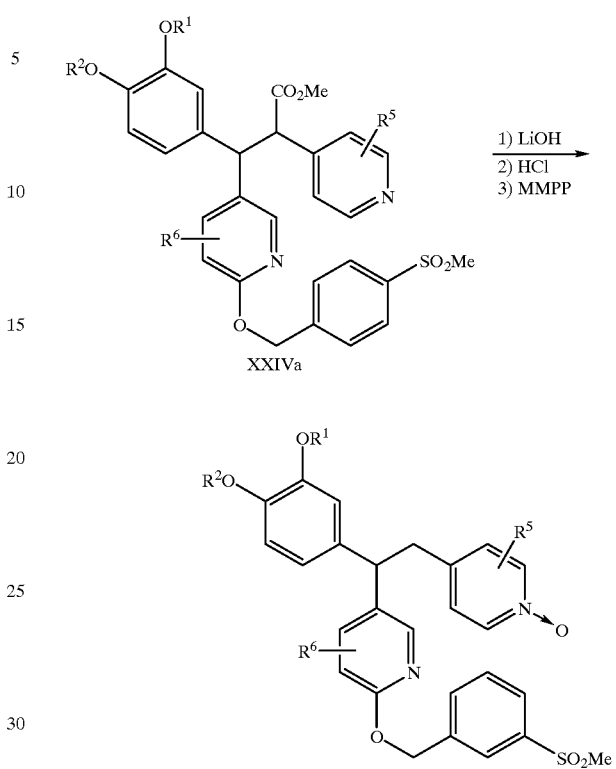
Representative compounds of the invention are shown below.

TABLE 1

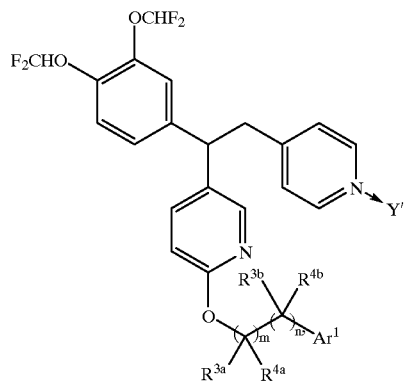

| Ex[a] | Y' | m | R³ᵃ | R⁴ᵃ | n | R³ᵇ | R⁴ᵇ | Ar¹ |
|---|---|---|---|---|---|---|---|---|
| 1 | O | 0 | — | — | 0 | — | — | 4-(trifluoromethoxy)phenyl |
| 2 | — | 0 | — | — | 0 | — | — | 4-(methoxycarbonyl)phenyl |
| 3 | O | 0 | — | — | 0 | — | — | 4-(methoxycarbonyl)phenyl |
| 4 | — | 0 | — | — | 0 | — | — | 4-(2-hydroxypropan-2-yl)phenyl |
| 5 | O | 0 | — | — | 0 | — | — | 4-(2-hydroxypropan-2-yl)phenyl |
| 6 | O | 0 | — | — | 0 | — | — | 4-nitrophenyl |
| 7 | O | 0 | — | — | 0 | — | — | 4-(methylsulphonylamino)phenyl |
| 8 | O | 0 | — | — | 0 | — | — | 4-(trifluoromethyl)phenyl |
| 9 | O | 0 | — | — | 0 | — | — | 3-(methylsulphonylamino)phenyl |
| 10 | O | 0 | — | — | 0 | — | — | 4-(2-propenyl)phenyl |
| 11 | O | 0 | — | — | 0 | — | — | 4-(2-propyl)phenyl |
| 12 | O | 0 | — | — | 0 | — | — | 4-(dimethylsulphonylamino)phenyl |
| 13[b] | O | 0 | — | — | 0 | — | — | 3-(hydroxymethyl)-4-(carboxyl)phenyl |
| 14 | O | 1 | H | H | 0 | — | — | phenyl |
| 15 | O | 1 | Me[c] | H | 0 | — | — | phenyl |
| 16 | O | 1 | H | H | 0 | — | — | 3,4-difluorophenyl |
| 17 | O | 1 | H | H | 0 | — | — | 4-(methylsulfonyl)phenyl |
| 18[d] | — | 1 | H | H | 0 | — | — | 3,5-difluorophenyl |
| 19[d] | — | 1 | H | H | 0 | — | — | 3,5-difluorophenyl |
| 20[d] | O | 1 | H | H | 0 | — | — | 3,5-difluorophenyl |
| 21[d] | O | 1 | H | H | 0 | — | — | 3,5-difluorophenyl |
| 22 | — | 1 | H | H | 1 | Me | Me | 4-fluorophenyl |
| 23 | O | 1 | H | H | 1 | Me | Me | 4-fluorophenyl |
| 24 | — | 1 | H | H | 1 | H | H | 4-fluorophenyl |
| 25 | O | 1 | H | H | 1 | H | H | 4-fluorophenyl |
| 26 | O | 1 | H | H | 0 | — | — | 4-(trifluoromethyl)phenyl |
| 27 | O | 1 | H | H | 0 | — | — | 4-(trifluoromethoxy)phenyl |
| 28 | O | 1 | Me | Me | 1 | H | H | phenyl |
| 29 | O | 1 | H | H | 0 | — | — | 2-thienyl |
| 30 | — | 1 | Me | Me | 0 | — | — | 4-fluorophenyl |
| 31 | O | 1 | Me | Me | 0 | — | — | 4-fluorophenyl |
| 32 | O | 1 | H | H | 0 | — | — | 4-fluorophenyl |
| 33 | O | 1 | H | H | 0 | — | — | 4-chlorophenyl |

[a]Unless specified, all the compounds are racemic mixture.
[b]Sodium salt.
[c]R, S mixture.
[d]Optically pure.

TABLE 2

[Structure: 4-(difluoromethoxy)-3-(difluoromethoxy)phenyl group connected via CH to a pyridine, with CH₂ linker to a pyridinium N-Y'; the pyridine bears an O-C(R³ᵃ)(R⁴ᵃ)-(C(R³ᵇ)(R⁴ᵇ))ₙ'-thiophene-(Rᵃ)₀₋₂ substituent]

| Y' | m | R³ᵃ | R⁴ᵃ | n' | R³ᵇ | R⁴ᵇ | Rᵃ |
|---|---|---|---|---|---|---|---|
| O | 0 | — | — | 0 | — | — | 4-(trifluoromethoxy) |
| — | 0 | — | — | 0 | — | — | 4-(methoxycarbonyl) |
| O | 0 | — | — | 0 | — | — | 4-(methoxycarbonyl) |
| — | 0 | — | — | 0 | — | — | 4-2-hydroxypropan-2-yl |
| O | 0 | — | — | 0 | — | — | 4-(2-hydroxypropan-2-yl) |
| O | 0 | — | — | 0 | — | — | 4-nitro |
| O | 0 | — | — | 0 | — | — | 4-(methylsulphonyl amino) |
| O | 0 | — | — | 0 | — | — | 4-(trifluoromethyl) |
| O | 0 | — | — | 0 | — | — | 5-(methylsulphonyl amino) |
| O | 0 | — | — | 0 | — | — | 4-(2-propenyl) |
| O | 0 | — | — | 0 | — | — | 4-(2-propyl) |
| O | 0 | — | — | 0 | — | — | 4-(dimethylsulphonyl amino) |
| O | 0 | — | — | 0 | — | — | 4-(hydroxymethyl)-5-(carboxyl) |
| O | 1 | H | H | 0 | — | — | — |
| O | 1 | Me | H | 0 | — | — | — |
| O | 1 | H | H | 0 | — | — | 4,5-difluoro |
| O | 1 | H | H | 0 | — | — | 4-(methylsulfonyl) |
| — | 1 | H | H | 0 | — | — | 3-fluoro |
| — | 1 | H | H | 0 | — | — | 4,5-difluoro |
| O | 1 | H | H | 0 | — | — | 4,5-dichloro |
| O | 1 | H | H | 0 | — | — | 5-fluoro |
| — | 1 | H | H | 1 | Me | Me | 4-fluoro |
| O | 1 | H | H | 1 | Me | Me | 4-fluoro |
| — | 1 | H | H | 1 | H | H | 5-fluoro |
| O | 1 | H | H | 1 | H | H | 4-fluoro |
| O | 1 | H | H | 0 | — | — | 4-(trifluoromethyl) |
| O | 1 | H | H | 0 | — | — | 4-(trifluoromethoxy) |
| O | 1 | Me | Me | 1 | H | H | — |
| O | 1 | H | H | 0 | — | — | — |
| — | 1 | Me | Me | 0 | — | — | 4-fluoro |
| O | 1 | Me | Me | 0 | — | — | 4-fluoro |
| O | 1 | H | H | 0 | — | — | 4-fluoro |
| O | 1 | H | H | 0 | — | — | 4-chloro |

TABLE 3

[Same as Table 2 but with thiazole (position 4) in place of thiophene]

| Y' | m | R³ᵃ | R⁴ᵃ | n' | R³ᵇ | R⁴ᵇ | Rᵃ |
|---|---|---|---|---|---|---|---|
| O | 0 | — | — | 0 | — | — | 4-(trifluoromethoxy) |
| — | 0 | — | — | 0 | — | — | 4-(methoxycarbonyl) |
| O | 0 | — | — | 0 | — | — | 4-(methoxycarbonyl) |
| — | 0 | — | — | 0 | — | — | 4-(2-hydroxypropan-2-yl) |
| O | 0 | — | — | 0 | — | — | 4-(2-hydroxypropan-2-yl) |
| O | 0 | — | — | 0 | — | — | 4-nitro |
| O | 0 | — | — | 0 | — | — | 4-(methylsulphonyl amino) |
| O | 0 | — | — | 0 | — | — | 4-(trifluoromethyl) |
| O | 0 | — | — | 0 | — | — | 5-(methylsulphonyl amino) |
| O | 0 | — | — | 0 | — | — | 4-(2-propenyl) |
| O | 0 | — | — | 0 | — | — | 4-(2-propyl) |
| O | 0 | — | — | 0 | — | — | 4-(dimethylsulphonyl amino) |
| O | 0 | — | — | 0 | — | — | 4-(hydroxymethyl)-5-(carboxyl) |
| O | 1 | H | H | 0 | — | — | — |
| O | 1 | Me | H | 0 | — | — | — |
| O | 1 | H | H | 0 | — | — | 4,5-difluoro |
| O | 1 | H | H | 0 | — | — | 4-(methylsulfonyl) |
| — | 1 | H | H | 0 | — | — | 4,5-dichloro |
| — | 1 | H | H | 0 | — | — | 5-fluoro |
| O | 1 | H | H | 0 | — | — | 4,5-dichloro |
| O | 1 | H | H | 0 | — | — | 5-fluoro |
| — | 1 | H | H | 1 | Me | Me | 4-fluoro |
| O | 1 | H | H | 1 | Me | Me | 4-fluoro |
| — | 1 | H | H | 1 | H | H | 4-fluoro |
| O | 1 | H | H | 1 | H | H | 4-fluoro |
| O | 1 | H | H | 0 | — | — | 4-(trifluoromethyl) |
| O | 1 | H | H | 0 | — | — | 4-(trifluoromethoxy) |
| O | 1 | Me | Me | 1 | H | H | — |
| O | 1 | H | H | 0 | — | — | — |
| — | 1 | Me | Me | 0 | — | — | 4-fluoro |
| O | 1 | Me | Me | 0 | — | — | 4-fluoro |
| O | 1 | H | H | 0 | — | — | 4-fluoro |
| O | 1 | H | H | 0 | — | — | 4-chloro |

TABLE 4

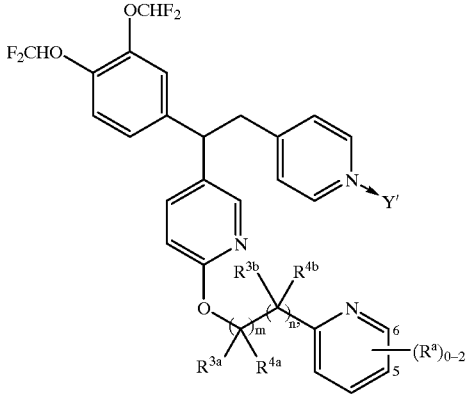

| Y' | m | R³ᵃ | R⁴ᵃ | n' | R³ᵇ | R⁴ᵇ | Rᵃ |
|---|---|---|---|---|---|---|---|
| O | 0 | — | — | 0 | — | — | 6-(trifluoromethoxy) |
| — | 0 | — | — | 0 | — | — | 6-(methoxycarbonyl) |
| O | 0 | — | — | 0 | — | — | 6-(methoxycarbonyl) |
| — | 0 | — | — | 0 | — | — | 6-(2-hydroxypropan-2-yl) |
| O | 0 | — | — | 0 | — | — | 6-(2-hydroxypropan-2-yl) |
| O | 0 | — | — | 0 | — | — | 6-nitro |
| O | 0 | — | — | 0 | — | — | 6-(methylsulphonyl amino) |
| O | 0 | — | — | 0 | — | — | 6-(trifluoromethyl) |
| O | 0 | — | — | 0 | — | — | 5-(methylsulphonyl amino) |
| O | 0 | — | — | 0 | — | — | 6-(2-propenyl) |
| O | 0 | — | — | 0 | — | — | 6-(2-propyl) |
| O | 0 | — | — | 0 | — | — | 6-(dimethylsulphonyl amino) |
| O | 0 | — | — | 0 | — | — | 5-(hydroxymethyl)-6-(carboxyl) |
| O | 1 | H | H | 0 | — | — | — |
| O | 1 | Me | H | 0 | — | — | — |
| O | 1 | H | H | 0 | — | — | 5,6-difluoro |
| O | 1 | H | H | 0 | — | — | 6-(methylsulfonyl) |
| — | 1 | H | H | 0 | — | — | 4,6-difluoro |
| — | 1 | H | H | 0 | — | — | 5,6-dichloro |
| O | 1 | H | H | 0 | — | — | 4,6-difluoro |
| O | 1 | H | H | 0 | — | — | 5,6-dimethyl |
| — | 1 | H | H | 1 | Me | Me | 6-fluoro |
| O | 1 | H | H | 1 | Me | Me | 6-fluoro |
| — | 1 | H | H | 1 | H | H | 6-fluoro |
| O | 1 | H | H | 1 | H | H | 6-fluoro |
| O | 1 | H | H | 0 | — | — | 6-(trifluoromethyl) |
| O | 1 | H | H | 0 | — | — | 6-(trifluoromethoxy) |
| O | 1 | Me | Me | 1 | H | H | — |
| O | 1 | H | H | 0 | — | — | — |
| — | 1 | Me | Me | 0 | — | — | 6-fluoro |
| O | 1 | Me | Me | 0 | — | — | 6-fluoro |
| O | 1 | H | H | 0 | — | — | 6-fluoro |
| O | 1 | H | H | 0 | — | — | 6-fluoro |

TABLE 5

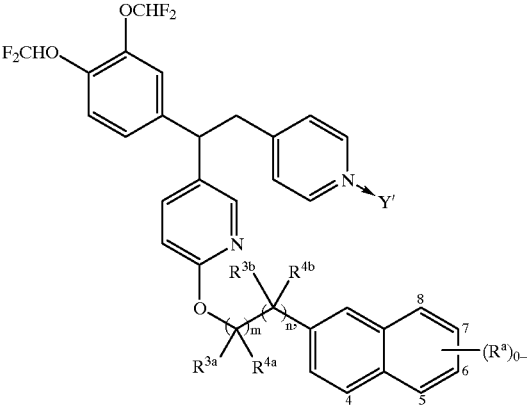

| Y' | m | R³ᵃ | R⁴ᵃ | n' | R³ᵇ | R⁴ᵇ | Rᵃ |
|---|---|---|---|---|---|---|---|
| O | 0 | — | — | 0 | — | — | 7-(trifluoromethoxy) |
| — | 0 | — | — | 0 | — | — | 7-(methoxycarbonyl) |
| O | 0 | — | — | 0 | — | — | 7-(methoxycarbonyl) |
| — | 0 | — | — | 0 | — | — | 7-(2-hydroxypropan-2-yl) |
| O | 0 | — | — | 0 | — | — | 7-(2-hydroxypropan-2-yl) |
| O | 0 | — | — | 0 | — | — | 7-nitro |
| O | 0 | — | — | 0 | — | — | 7-(methylsulphonyl amino) |
| O | 0 | — | — | 0 | — | — | 7-(trifluoromethyl) |
| O | 0 | — | — | 0 | — | — | 6-(methylsulphonyl amino) |
| O | 0 | — | — | 0 | — | — | 7-(2-propenyl) |
| O | 0 | — | — | 0 | — | — | 7-(2-propyl) |
| O | 0 | — | — | 0 | — | — | 7-(dimethylsulphonyl amino) |
| O | 0 | — | — | 0 | — | — | 6-(hydroxymethyl)-7-(carboxyl) |
| O | 1 | H | H | 0 | — | — | — |
| O | 1 | Me | H | 0 | — | — | — |
| O | 1 | H | H | 0 | — | — | 6,7-difluoro |
| O | 1 | H | H | 0 | — | — | 7-(methylsulfonyl) |
| — | 1 | H | H | 0 | — | — | 6,7-difluoro |
| — | 1 | H | H | 0 | — | — | 5,7-difluoro |
| O | 1 | H | H | 0 | — | — | 5-fluoro |
| O | 1 | H | H | 0 | — | — | 6-fluoro |
| — | 1 | H | H | 1 | Me | Me | 7-fluoro |
| O | 1 | H | H | 1 | Me | Me | 7-fluoro |
| — | 1 | H | H | 1 | H | H | 7-fluoro |
| O | 1 | H | H | 1 | H | H | 7-fluoro |
| O | 1 | H | H | 0 | — | — | 7-(trifluoromethyl) |
| O | 1 | H | H | 0 | — | — | 7-(trifluoromethoxy) |
| O | 1 | Me | Me | 1 | H | H | — |
| O | 1 | H | H | 0 | — | — | — |
| — | 1 | Me | Me | 0 | — | — | 7-fluoro |
| O | 1 | Me | Me | 0 | — | — | 7-fluoro |
| O | 1 | H | H | 0 | — | — | 7-fluoro |
| O | 1 | H | H | 0 | — | — | 7-chloro |

TABLE 6

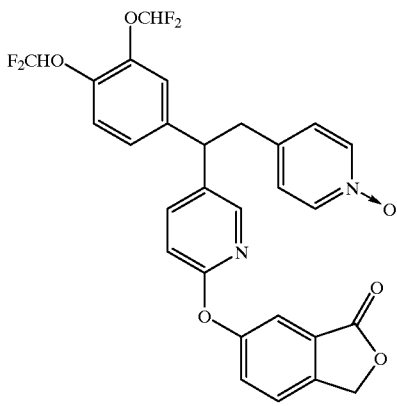

Ex 34

TABLE 7

IN VITRO POTENCY OF SOME REPRESENTATIVE PDE 4 INHIBITORS.

| Ex. | $IC_{50}$ (nM) GST-Met 248 PDE 4a |
|---|---|
| 1 | 2.85 |
| 16 | 1.43 |
| 23 | 3.2 |
| 28 | 0.2 |

ASSAYS DEMONSTRATING BIOLOGICAL ACTIVITY
LPS AND FMLP-INDUCED TNF-α AND $LTB_4$ ASSAYS IN HUMAN WHOLE BLOOD

Whole blood provides a protein and cell-rich milieu appropriate for the study of biochemical efficacy of anti-inflammatory compounds such as PDE 4-selective inhibitors. Normal non-stimulated human blood does not contain detectable TNF-α and $LTB_4$. Upon stimulation with LPS, activated monocytes expresss and secrete TNF-α up to 8 hours and plasma levels remain stable for 24 hours. Published studies have shown that inhibition of TNF-α by increasing intracellular cAMP via PDE 4 inhibition and/or enhanced adenylyl cyclase activity occurs at the transcriptional level. $LTB_4$ synthesis is also sensitive to levels of intracellular cAMP and can be completely inhibited by PDE 4-selective inhibitors. As there is little $LTB_4$ produced during a 24 hour LPS stimulation of whole blood, an additional LPS stimulation followed by tMLP challenge of human whole blood is necessary for $LTB_4$ synthesis by activated neutrophils. Thus, using the same blood sample it is possible to evaluate the potency of a compound on two surrogate markers of PDE 4 activity in the whole blood.

Fresh blood was collected in heparinized tubes by venipuncture from healthy human volunteers (male and female). These subjects had no apparent inflammatory conditions and had not taken any NSAIDs for at least 4 days prior to blood collection. Five hundred μL aliquots of blood were pre-incubated with either 2 μL of vehicle (DMSO) or 2 μL test compound at varying concentrations for 15 minutes at 37° C. This was followed by the addition of either 10 μL vehicle (PBS) as blanks or 10 μL LPS (1 μg/ml final concentration, Sigma Chem, #L-2630 from *E. coli*, serotype 0111:B4; diluted in 0.1% w/v BSA (in PBS)). After 24 hours of incubation at 37° C., another 10 μL of PBS (blank) or 10 μL of LPS (1 μg/ml final concentration) was added to blood and incubated for 30 minutes at 37° C. The blood was then challenged with either 10 μL of PBS (blank) or 10 μL of fMLP (1 μM final concentration, Sigma Chem #F-3506; diluted in 1% w/v BSA (in PBS)) for 15 minutes at 37° C. The blood samples were centrifuged at 1500×g for 10 minutes at 4° C. to obtain plasma. A 50 μL aliquot of plasma was mixed with 200 μL methanol for protein precipitation and centrifuged as above. The supernatant was assayed for $LTB_4$ using an enzyme immunoassay kit (Cayman Chemicals #520111) according to the manufacturer's procedure. TNF-α was assayed in diluted plasma (in PBS) using an ELISA kit (Cistron Biotechnology) according to manufacturer's procedure.

ANTI-ALLERGIC ACTIVITY IN VIVO

Compounds of the invention have been tested for effects on an IgE-mediated allergic pulmonary inflammation induced by inhalation of antigen by sensitised guinea pigs. Guinea pigs were initially sensitised to ovalbumin under mild cyclophosphamide-induced immunosuppression, by intraperitoneal injection of antigen in combinations with aluminium hydroxide and pertussis vaccine. Booster doses of antigen were given two and four weeks later and at six weeks, animals were challenged with aerosolised ovalbumin whilst under cover of an intraperitoneally administered anti-histamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigen challenge, lead to a significant reduction in the eosinophilia and the accumulation of other inflammatory leukocytes. There was also less inflammatory damage in the lungs of animals treated with compounds of the Examples.

SPA BASED PDE ACTIVITY ASSAY PROTOCOL

Compounds which inhibit the hydrolysis of cAMP to AMP by the type-IV cAMP-specific phosphodiesterases were screened in 96-well plate format as follows:

In a 96 well-plate at 30° C. was added the test compound (dissolved in 2 μl DMSO), 188 ml of substrate buffer containing [2,8-$^3$H] adenosine 3',5'-cyclic phosphate (cAMP, 100 nM to 50 μM), 10 mM $MgCl_2$, 1 mM EDTA, 50 mM Tris, pH 7.5. The reaction was initiated by the addition of 10 ml of human recombinant PDE-IV (the amount was controlled so that ~10% product was formed in 10 min.). The reaction was stopped after 10 min. by the addition of 1 mg of PDE-SPA beads (Amersham). The product AMP generated was quantified on a Microbeta 96-well plate counter. The signal in the absence of enzyme was defined as the background. 100% activity was defined as the signal detected in the presence of enzyme and DMSO with the background subtracted. Percentage of inhibition was calculated accordingly. $IC_{50}$ value was approximated with a non-linear regression fit using the standard 4-parameter/multiple binding sites equation from a ten point titration.

$IC_{50}$ values shown in Table 7 were determined with 100 nM cAMP using the purified GST fusion protein of the human recombinant phosphodiesterase IVa (met-248) produced from a baculovirus/Sf-9 expression system.

The invention will now be illustrated by the following non-limiting examples in which, unless stated otherwise:

(i) all operations were carried out at room or ambient temperature, that is, at a temperature in the range 18–25° C.; evaporation of solvent was carried out using a rotary evaporator under reduced pressure (600–4000 pascals: 4.5–30 mm. Hg) with a bath temperature of up to 60° C.; the course of reactions was followed by thin layer chromatography (TLC) and reaction times are given for illustration only; melting points are uncorrected and 'd' indicates decomposition; the melting points given are those obtained for the materials prepared as described; polymorphism may result in isolation of materials with different melting points in some preparations; the structure and purity of all final products were assured by at least one of the following techniques: TLC, mass spectrometry, nuclear magnetic resonance (NMR) spectrometry or microanalytical data; yields are given for illustration only; when given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent; conventional abbreviations used for signal shape are: s. singlet; d. doublet; t. triplet; m. multiplet; br. broad; etc.: in addition "Ar" signifies an aromatic signal; chemical symbols have their usual meanings; the following abbreviations have also been used v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

EXAMPLE 1

4-{2-[3,4-BIS(DEFLUOROMETHOXY)PHENYL]-2-{6-[4-(TRIFLUOROMETHOXY)PHENOXY]-3-PYRIDYL}ETHYL}PYRIDINE-N-OXIDE

Step 1
[3,4-Bis(difluoromethoxy)phenyl]-{6-[4-(trifluoromethoxy)phenoxy]-3-pyridyl}methanone To a 0° C. solution of 4-trifluoromethoxyphenol (0.33 mL, 2.54 mmol) in 5 mL of anhydrous DMF, was added dropwise 2.54 mL (2.54 mmol) of a 1.0 M solution of potassium t-butoxide in THF followed by 500 mg (1.27 mmol) of intermediate 1. The resulting orange solution was stirred 20 h at room temperature, quenched by the addition of a saturated aqueous NH4Cl solution and diluted with Et2O. The organic layer was washed with a 0.5 N NaOH solution, water and brine, dried over $MgSO_4$ and concentrated under reduced pressure. The residue was purified by flash chromatography on silica gel (10% Ethyl acetate/toluene) to afford the desired aryl ether as an oil (484 mg, 77%).

Step 2
[3,4-Bis(difluoromethoxy)phenyl]-{6-[4-(trifluoromethoxy)phenoxy]-3-pydidyl}methanol To a 0° C. solution of ketone (484 mg, 0.985 mmol) from Step 1 above in 12 mL of a 5:1 mixture of THE: MeOH, was added slowly 75 mg (1.97 mmol) of NaBH4. The resulting solution was stirred 2.5 h at 0° C., quenched with a saturated aqueous NH4Cl solution and diluted with ethyl acetate. The organic layer was washed with brine, dried over $MgSO_4$ and concentrated under reduced pressure. The residue was used directly for the next step without any purification.

Step 3
[3,4-Bis(difluoromethoxy)phenyl]-{6-[4-(trifluoromethoxy)phenoxy]-3-pyridyl}chloromethane To a 0° C. solution of alcohol (500 mg, 1.01 mmol) from Step 2 above and i-Pr2NEt (400 mL, 2.22 mmol) in 14 mnL of a 1:1 mixture of toluene:THF, was slowly added $SOCl_2$ (100 mL, 1.11 mmol). The resulting yellow solution was stirred 30 minutes at 0° C., quenched with water and diluted with ethyl acetate. The organic layer was washed with brine, dried over $MgSO_4$ and concentrated under reduced pressure. The residue was used directly for the next step without any purification.

Step 4
4-{1-Carbethoxy-2-[3,4-bis(difluoromethoxy)phenyl]-2-{6-[4-(trifluoromethoxy)phenoxy]-3-pyridyl}ethyl}pyridine To a solution of ethyl 4-pyridyl acetate (502 mg, 3.03 mmol) and HMPA (530 mL, 3.03 mmol) in 12 mL of THF, was slowly added 6.1 mL (3.03 mmol) of a 0.5 M solution of KHMDS in toluene. The resulting cloudy orange solution was stirred 10 minutes at room temperature followed by the addition of a THE (6 mL) solution of the crude chloride from Step 3 above. The resulting mixture was stirred 30 minutes at room temperature, quenched with a saturated aqueous NH4Cl solution and diluted with ethyl acetate. The organic layer was washed with water and brine, dried over $MgSO_4$ and concentrated under reduced pressure. The residue was used directly for the next step without any purification.

Step 5
4-{2-[3,4-Bis(difluoromethoxy)phenyl]-2-{6-[4-(trifluoromethoxy)phenoxy]-3-pyridyl}ethyl}pyridine To a solution of the crude ester from Step 4 above in 25 mL of a 3:1:1 mixture of THF:MeOH:water, was added 5.1 mL (10.3 mmol) of a 2 N solution of LiOH. The resulting solution was stirred at 65° C. for 1.5 h, cooled down to room temperature followed by the addition of 10 mL of a 1.0 N HCl solution. The resulting mixture was rotovaped down to evaporate MeOH and the aqueous residue was diluted with ethyl acetate. The organic layer was washed with water and brine, dried over $MgSO_4$ and concentrated under reduced pressure. The residue was purified by flash chromatography on silica gel (50% Ethyl acetate/hexane) to afford the desired pyridine as an oil (380 mg, 68% from Step 2).

Step 6
4-{2-[3,4-Bis(difluoromethoxy)phenyl]-2-{6-[4-(trifluoromethoxy)phenoxy]-3-pyridyl}ethyl}pyridine-N-oxide To a solution of 4-{2-[3,4-bis(difluoromethoxy)phenyl]-2-{6-[4-(trifluoromethoxy)phenoxy]-3-pyridyl}ethyl}pyridine (340 mg, 0.598 mmol) from Step 5 above in a mixture of 6 mL of $CH_2Cl_2$ and 0.6 mL of MeOH, was added MMPP (222 mg, 0.359 mmol) in one portion. The mixture was stirred 24 h at room temperature and the reaction was completed with an other 50 mg of MMPP. The reaction was quenched with a saturated aqueous NaHCO3 solution and diluted with $CH_2Cl_2$. The organic layer was washed with brine, dried over $MgSO_4$ and concentrated under reduced pressure. The residue was purified by flash chromatography on silica gel (5% MeOH/CH2Cl2) to afford the title compound as an amorphous solid (340 mg, 97%).

$^1$H NMR (500 MHz, Acetone-d6) δ 8.10 (d, 1H), 7.94 (m, 2H), 7.89 (m, 1H), 7.41 (s, 1H), 7.36–7.33 (d, 2H), 7.28 (d, 1H), 7.23–7.18 (m, 4H), 6.98 (d, 1H), 6.95 (t, 1H), 6.93 (t, 1H), 4.56 (t, 1H), 3.49 (m, 2H).

EXAMPLE 2

4-{2-[3,4-BIS(DIFLUOROMETHOXY)PHENYL]-2-{6-[4-(METHOXYCARBONYL)PHENOXY]-3-PYRIDYL}ETHYL}PYRIDINE

Step 1
[3,4-Bis(difluoromethoxy)phenyl]-{6-[4-(methoxycarbonyl)phenoxy]-3-pyridyl}methanone To a 0° C. solution of intermediate 1 (507 mg, 1.29 mmol) and 4-methoxycarbonylphenol (391 mg, 2.6 mmol) in 5 mL of anhydrous DMF, was added dropwise 2.6 mL (2.6 mmol) of a 1.0 M solution of potassium t-butoxide. The resulting orange solution was stirred 15 h at room temperature, quenched by the addition of a saturated aqueous $NH_4Cl$ solution and diluted with $Et_2O$. The organic layer was washed with 0.1 N NaOH solution, water and brine, dried over $MgSO_4$ and concentrated under reduced pressure. The residue was used directly for the next step without any purification.

Step 2
[3,4-Bis(difluoromethoxy)phenyl]-{6-[4-(methoxycarbonyl)phenoxy]-3-pyridyl}methanol To a 0° C. solution of ketone (540 mg, 1.16 mmol) from Step 1 in 12 mL of a 5:1 mixture of THF: MeOH, was added slowly 88 mg (2.3 mmol) of $NaBH_4$. The resulting solution was stirred 30 minutes at 0° C., quenched with a saturated aqueous $NH_4Cl$ solution and diluted with ethyl acetate. The organic layer was washed with brine, dried over $MgSO_4$ and concentrated under reduced pressure. The residue was used directly for the next step without any purification.

Step 3
[3,4-Bis(difluoromethoxy)phenyl]-{6-[4-(methoxycarbonyl)phenoxy]-3-pyridyl}chloromethane To a 0° C. solution of alcohol (535 mg, 1.14 mmol) from step 2 and i-$Pr_2NEt$ (436 mL, 2.5 mmol) in 10 mL of anhydrous toluene, was slowly added $SOCl_2$ (145 mnL, 2.0 mmol). The resulting yellow solution was stirred 30 minutes at 0° C., 10 minutes at room temperature, quenched with water and diluted with ethyl acetate. The organic layer was washed with brine, dried over $MgSO_4$ and concentrated under reduced pressure. The residue was used directly for the next step without any purification.

Step 4
4-{1-Carbethoxy-2-[3,4-bis(difluoromethoxy)phenyl]-2-{6-[4-(methoxycarbonyl)phenoxy]-3-pyridyl}ethyl}pybidine To a solution of ethyl 4-pyridyl acetate (564 mg, 3.42 mmol) and HMPA (594 mL, 3.42 mmol) in THF, was slowly added 6.8 mL (3.42 mmol) of a 0.5 M solution of KHMDS in toluene. The resulting cloudy orange solution was stirred 10 minutes at room temperature followed by the addition of a THF (8 mL) solution of the crude chloride from Step 3. The resulting mixture was stirred 30 minutes at room temperature, quenched with a saturated aqueous $NH_4Cl$ solution and diluted with ethyl acetate. The organic layer was washed with water and brine, dried over $MgSO_4$ and concentrated under reduced pressure. The residue was used directly for the next step without any purification.

Step 5
4-{2-[3,4-Bis(difluoromethoxy)phenyl[-2-{6-[4-(methoxycarbonyl)phenoxy]-3-pyridyl}ethyl}pyridine To a solution of the crude ester from Step 4 above in 25 mL of a 3:1:1 mixture of THF:MeOH:water, was added 5.1 mL (10.3 mmol) of a 2 N solution of LiOH. The resulting solution was stirred at 65° C. for 1.5 h, cooled down to room temperature followed by the addition of 11 mL of a 1.0 N HCl solution. The resulting mixture was rotovaped down to evaporate MeOH and the aqueous residue was diluted with ethyl acetate. The organic layer was washed with water and brine, dried over $MgSO_4$ and concentrated under reduced pressure. The residue was dissolved in ethyl acetate and treated with $CH_2N_2$ and monitored by TLC until all the carboxylic acid have been esterified. The solution was concentrated under reduced pressure and the residue was purified by flash chromatography on silica gel (70% Ethyl acetate/hexane) to afford the title compound as a viscous oil (432 mg, 62% from Step 1).

$^1H$ NMR (300 MHz, Acetone-d6) δ 8.38 (d, 2H), 8.14 (d, 1H), 8.05–7.99 (m, 2H), 7.93 (dd, 1H), 7.43 (d, 1H), 7.36 (dd, 1H), 7.28 (d, 1H), 7.22–7.14 (m, 4H), 7.01 (d, 1H), 6.96 (t, 1H), 6.94 (t, 1H), 4.63 (t, 1H), 3.87 (s, 3H), 3.50 (d, 2H).

EXAMPLE 3

4-{2-[3,4-BIS(DIFLUOROMETHOXY)PHENYL]-2-{6-[4-(METHOXYCARBONYL)PHENOXY]-3-PYRIDYL}ETHYL}PYRIDINE-N-OXIDE

To a solution of 4-{2-[3,4-bis(difluoromethoxy)phenyl]-2-{6-[4-(methoxycarbonyl)phenoxy]-3-pyridyl}ethyl}pyridine from Example 1 (249 mg, 0.46 mmol) in a mixture of 5 mL of $CH_2Cl_2$ and 0.5 mL of MeOH, was added MMPP (171 mg, 0.28 mmol) in one portion. The mixture was stirred 24 h at room temperature, quenched with a saturated aqueous $NaHCO_3$ solution and diluted with $CH_2Cl_2$. The organic layer was washed with brine, dried over $MgSO_4$ and concentrated under reduced pressure. The residue was purified by flash chromatography on silica gel (Gradient 20% to 40% EtOHiethyl acetate) to afford the title compound as a viscous oil (260 mg, 71%).

$^1H$ NMR (400 MHz, Acetone-d6) δ 8.15 (d, 1H), 8.05–8.01 (m, 2H), 7.98–7.92 (m, 3H), 7.44 (d, 1H), 7.36 (dd, 1H), 7.29 (d, 1H), 7.23–7.16 (m, 4H), 7.03 (d, 1H), 6.97 (t, 1H), 6.94 (t, 1H), 4.60 (t, 1H), 3.89 (s, 3H), 3.50 (dd, 2H).

EXAMPLE 4

4-{2-[3,4-BIS(DIFLUOROMETHOXY)PHENYL]-2-{6-[4-(2-HYDROXYPROPAN-2-YL)PHENOXY]-3-PYRIDYL}ETHYL}PYRIDINE

A suspension of dry $CeCl_3$ (2.7 g, 11.0 mmol) in 50 mL of THF was refluxed 1 h, cooled to 0° C. and treated with 3.7 mL (11.0 mmol) of a 3.0 M solution of MeMgBr in $Et_2O$. The resulting mixture was stirred 1 h at 0° C., cooled to −40° C. followed by the addition of a THF (10 mL) solution of 4-{2-[3,4-bis(difluoromethoxy)phenyl]-2-{6-[4-(methoxycarbonyl)phenoxy]-3-pyridyl}ethyl}pyridine. After stirring 30 minutes at −40° C., the reaction was quenched with a saturated aqueous $NH_4Cl$ solution and diluted with ethyl acetate. The organic layer was washed with water and brine, dried over $MgSO_4$ and concentrated under reduced pressure. The residue was purified by flash chromatography on silica gel (Gradient 5% to 10% EtOH/ethyl acetate) to afford the title compound as a foam (1.1 g, 99%).

$^1H$ NMR (300 MHz, Acetone-$d_6$) δ 8.38 (s, 2H), 8.07 (d, 1H), 7.84 (dd, 1H), 7.55–7.49 (m, 2H), 7.40 (s, 1H), 7.34 (dd, 1H), 7.26 (d, 1H), 7.22–7.16 (m, 2H), 7.03–6.96 (m, 2H), 6.94 (t, 1H), 6.93 (t, 1H), 6.88 (d, 1H), 4.59 (t, 1H), 4.00 (s, 1H), 3.5 (d, 2H), 1.50 (s, 6H).

EXAMPLE 5

4-{2-[3,4-BIS(DIFLUOROMETHOXY)PHENYL]-2-{6-[4-(2-HYDROXYPROPAN-2-YL)PHENOXY]-3-PYRIDYL}ETHYL}PYRIDINE-N-OXIDE

Following the procedure described in Example 3 but using 4-{2-[3,4-bis(difluoromethoxy)phenyl]-2-{6-[4-(2- hydroxypropan-2-yl)phenoxy]-3-pyridyl}ethyl}pyridine as starting material, the title compound was obtained as a white foam (23 mg, 77%).

$^1$H NMR (400 MHz, Acetone-$d_6$) δ 8.08 (d, 1H), 7.98–7.94 (m, 2H), 7.85 (dd, 1H), 7.55–7.50 (m, 2H), 7.42 (s, 1H), 7.35 (dd, 1H), 7.27 (d, 1H), 7.21 (d, 2H), 7.03–6.97 (m, 2H), 6.96 (t, 1H), 6.94 (t, 1H), 6.90 (d, 1H), 4.55 (t, 1H), 3.50 (d, 2H), 1.51 (s, 6H).

EXAMPLE 6

4-{2-[3,4-BIS(DIFLUOROMETHOXY)PHENYL]-2-[6-(4-NITROPHENOXY)-3-PYRIHDYL]ETHYL}PYRIDINE-N-OXIDE

Step 1
[3,4-Bis(difluoromethoxy)phenyl]-[6-(4-nitrophenoxy)-3-pyridyl]methanone

Following the procedure described in Example 1, Step 1 but substituting 4-nitrophenol for 4-trifluoromethoxyphenol, the desired aryl ether was obtained as an oil (1.02 mg, 89%).

Step 2
[3,4-Bis(difluoromethoxy)phenyl]-[6-(4-nitrophenoxy)-3-pyridyl]methanol

The procedure for the reduction of the ketone described in Example 1, Step 2 was applied using the product of step 1 above as starting material. The alcohol obtained was used directly for the next step without any purification.

Step 3
[3,4-Bis(difluoromethoxy)phenyl]-[6-(4-nitrophenoxy)-3-pyridyl]chloromethane The procedure for the formation of the chloride described in Example 1, Step 3 was applied using the product of Step 2 above as starting material. The chloride obtained was used directly for the next step without any purification.

Step 4
4-{1-Carbethoxy-2-[3,4-bis(difluoromethoxy)phenyl]-2-[6-(4-nitrophenoxy)-3-pyridyl]ethyl}pyridine The procedure for the alkylation with ethyl 4-pyridylacetate described in Example 1, Step 4 was applied using the product of Step 3 above as starting material. The ethyl ester obtained was used directly for the next step without any purification.

Step 5
4-{2-[3,4-bis(difluoromethoxy)phenyl]-2-[6-(4-nitrophenoxy)-3-pyridyl]ethyl}pyridine The procedure for the hydrolysis/decarboxylation described in Example 1, Step 5 was applied using the product of Step 4 above as starting material. The protected aminopyridine was obtained as an oil (710 mg, 60% for 4 steps).

Step 6
4-{2-[3,4-Bis(difluoromethoxy)phenyl]-2-[6-(4-nitrophenoxy)-3-pyridy]ethyl}pyridine-N-oxide The procedure for the oxidation of the pyridine group described in Example 1, Step 6 was applied using the product of Step 5 above as starting material. The title compound was obtained as an oil (103 mg, 91%).

$^1$H NMR (500 MHz, Acetone-$d_6$) δ 8.27 (d, 2H), 8.19 (s, 1H), 7.99–7.94 (m, 3H), 7.44 (s, 1H), 7.38–7.19 (m, 4H), 7.10 (d, 2H), 6.96 (t, 1H), 6.94 (t, 1H), 4.60 (t, 1H), 3.51 (m, 2H).

EXAMPLE 7

4-{2-[3,4-BIS(DIFLUOROMETHOXY)PHENYL]-2-{6-[4-(METHYLSULFONYLAMINO)PHENOXY]-3-PYRIDYL}ETHYL}PYRIDINE-N-OXIDE

Step 1
4-{2-[3,4-bis(difluoromethoxy)phenyl]-2-[6-(4-aminophenoxy)-3-pyridyl]ethyl}pyridine To a solution of 4-{2-[3,4-bis(difluoromethoxy)phenyl]-2-[6-(4-nitrophenoxy)-3-pyridyl]ethyl}pyridine (600 mg, 1.13 mmol) from Example 6, Step 5 in 20 mL EtOH, was added 120 mg of Pd/C 10% and the resulting mixture was stirred 20 h under $H_2$ atmosphere. The reaction was filtered on celite, washed with ethyl acetate and concentrated under reduced pressure. The residue was purified by flash chromatography on silica gel (10% EtOH/Ethyl acetate) to afford the amine as an oil (500 mg, 88%).

Step 2
4-{2-[3,4-Bis(difluoromethoxy)phenyl]-2-{6-[4-(methylsulfonylamino)phenoxy]-3-pyridyl}ethyl}pyridine To a 0° C. solution of amine from Step 1 above (200 mg, 0.4 mmol) in 6 mL of $CH_2Cl_2$ was added 0.28 mL (2.0 mmol) of $Et_3N$ followed by 0.11 mL (1.4 mmol) of methylsulfonyl chloride. The solution was stirred at 0° C. for 1.5 h, quenched with water and diluted with $CH_2Cl_2$. The organic layer was washed with brine, dried over $MgSO_4$ and concentrated under reduced pressure. The residue was dissolved in 10 mL of a 1:1:1 mixture of THF:MeOH: 1 N $K_2CO_3$, stirred for 3.5 h at room temperature, quenched with a saturated aqueous $NH_4Cl$ solution and diluted with ethyl acetate. The organic layer was washed with brine, dried over $MgSO_4$ and concentrated under reduced pressure. The residue was purified by flash chromatography on silica gel (100% ethyl acetate) to afford the methyl sulfonamide as a foam (114 mg, 51%).

Step 3
4-{2-[3,4-Bis(difluoromethoxy)phenyl]-2-{6-[4-(methylsulfonylamino)phenoxy]-3-pyridyl}ethyl}pyridine-N-oxide The procedure for the oxidation of the pyridine group described in Example 1, Step 6 was applied using the product of Step 2 above as starting material. The title compound was obtained as a foam (85 mg, 73%).

$^1$H NMR (500 MHz, Acetone-$d_6$) δ 8.71 (brs, 1H), 8.08 (d, 1H), 7.97 (d, 2H), 7.85 (dd, 1H), 7.41 (d, 1H), 7.37–7.33 (m, 3H), 7.28 (d, 1H), 7.20 (d, 2H), 7.10–6.78 (m, 5H), 4.54 (t, 1H), 3.49 (m, 2H), 2.97 (s, 3H).

EXAMPLE 8

4-{2-[3,4-BIS(DIFLUOROMETHOXY)PHENYL]-2-{6-[4-(TRIFLUOROMETHYL)PHENOXY]-3-PYRIDYL}ETHYL}PYRIDINE-N-OXIDE

Following the procedure described in Example 1 but substituting 4-trifluoromethylphenol for 4-trifluoromethoxyphenol, the title compound was obtained as a white foam (270 mg).

$^1$H NMR (500 MHz, Acetone-$d_6$) d 8.14 (d, 1H), 7.98–7.92 (m, 3H), 7.73 (d, 2H), 7.43 (d, 1H), 7.35 (dd, 1H), 7.29 (m, 3H), 7.19 (d, 2H), 7.03 (d, 1H), 6.96 (t, 1H), 6.94 (t, 1H), 4.58 (t, 1H), 3.50 (m, 2H).

EXAMPLE 9

4-{2-[3,4-BIS(DIFLUOROMETHOXY)PHENYL]-2-{6-[3-(METHYLSULFONYLAMINO)PBENOXY]-3-PYRIDYL}ETHYL}PYRIDINE-N-OXIDE

Following the procedure described in Example 1, Step 1 but substituting 3-nitrophenol for 4-trifluoromethoxyphenol, the desired aryl ether was obtained as an oil (1.06 g, 92%).

Step 2
[3,4-Bis(difluoromethoxy)phenyl]-[6-(3-nitrophenoxy)-3-pyridyl]methanol

The procedure for the reduction of the ketone described in Example 1, Step 2 was applied using the product of Step 1 above as starting material. The alcohol obtained was used directly for the next step without any purification.

Step 3
[3,4-Bis(difluoromethoxysphenyl]-[6-(3-nitrophenoxy)-3-pyridyl]chloromethane The procedure for the formation of the chloride described in Example 1, Step 3 was applied using the product of Step 2 above as starting material. The chloride obtained was used directly for the next step without any purification.

Step 4
4-{1-Carbethoxy-2-[3,4-bis(difluoromethoxy)phenyl]-2-[6-(3-nitrophenoxy)-3-pyridyl]ethyl}pyridine The procedure for the alkylation with ethyl 4-pyridylacetate described in Example 1, Step 4 was applied using the product of Step 3 above as starting material. The ethyl ester obtained was used directly for the next step without any purification.

Step 5
4-{2-[3,4-bis(difluoromethoxy)phenyl]-2-[6-(4-nitrophenoxy)-3-pyridyl]ethyl}pyridine The procedure for the hydrolysis/decarboxylation described in Example 1, Step 5 was applied using the product of Step 4 above as starting material. The protected aminopyridine was obtained as an oil (410 mg, 34% for 4 steps).

Step 6
4-{2-[3,4-bis(difluoromethoxy)phenyl]-2-[6-(4-aminophenoxy)-3-pyridyl]ethyl}pyridine The procedure for the reduction of the nitro group described in Example 7, Step 1 was applied using the product of Step 5 above as starting material. The amine was obtained as an oil (185 mg, 48%).

Step 7
4-{2-[3,4-Bis(difluoromethoxy)phenyl]-2-{6-[3-(methylsulfonylamino)phenoxy]-3-pyddyl}ethyl}pyridine The procedure for the sulfonylation of the amine group described in Example 7, Step 2 was applied using the product of Step 6 above as starting material. The sulfonamide was obtained as an oil (80 mg, 37%).

Step 8
4-{2-[3,4-Bis(difluoromethoxy)phenyl]-2-{6-[3-(methylsulfonylamino)phenoxy]-3-pyridyl}ethyl}pyridine-N-oxide The procedure for the oxidation of the pyridine group described in Example 1, Step 6 was applied using the product of Step 7 above as starting material. The title compound was obtained as a foam (55 mg, 67%).

$^1$H NMR (500 MHz, Acetone-$d_6$) δ 9.04 (brs, 1H), 8.21 (d, 1H), 8.10 (d, 2H), 7.98 (dd, 1H), 7.54 (s, 1H), 7.46 (m, 3H), 7.40 (d, 1H), 7.31 (d, 2H), 7.25 (dd, 1H), 7.22–6.90 (m, 5H), 4.67 (t, 1H), 3.61 (m, 2H), 3.12 (s, 3H).

EXAMPLE 10

4-{2-[3,4-BIS(DIFLUOROMETHOXY)PHENYL]-2-{6-[4-(2-PROPENYL)PHENOXY]-3-PYRIDYL}ETHYL}PYRIDINE-N-OXIDE

To a solution of 148 mg (0.26 mmol) of 4-{2-[3,4-bis(difluoromethoxy)phenyl]-2-{6-[4-(2-hydroxypropan-2-yl)phenoxy]-3-pyridyl}ethyl}pyridine-N-oxide (Example 5) in 3.0 mL of $CH_2Cl_2$ was added 85 mg (0.45 mmol) of p-toluenesulf6nic acid at room temperature. The solution was stirred 2 days at room temperature, quenched with a saturated aqueous $NaHCO_3$ solution and diluted with $CH_2Cl_2$. The organic layer was washed with brine, dried over $MgSO_4$ and concentrated under reduced pressure. The residue was purified by flash chromatography on silica gel (Gradient 20% to 30% EtOH/ethyl acetate) to afford the title compound as a foam (98 mg, 68%).

$^1$H NMR (500 MHz, Acetone-$d_6$) δ 8.09 (d, 1H), 7.95 (d, 2H), 7.86 (dd, 1H), 7.54–7.50 (m, 2H), 7.41 (s, 1H), 7.34 (dd, 1H), 7.27 (d, 1H), 7.18 (d, 2H), 7.06–7.03 (m, 2H), 6.95 (t, 1H), 6.93 (t, 1H), 6.93 (d, 1H), 5.38 (s, 1H), 5.07 (s, 1H), 4.55 (t, 1H), 3.5 (dd, 2H), 2.12 (s, 3H).

EXAMPLE 11

4-{2-[3,4-BIS(DIFLUOROMETHOXY)PHENYL]-2-{6-[4-(2-PROPYL)PHENOXY]-3-PYRIDYL}ETHYL}PYRIDINE-N-OXIDE

Following the procedure described in Example 1 but substituting 4-(2-propyl)phenol for 4-trifluoromethoxyphenol, the title compound was obtained as a white foam (233 mg).

$^1$H NMR (300 MHz, Acetone-$d_6$) δ 8.08 (d, 1H), 7.95 (m, 2H), 7.83 (dd, 1H), 7.41 (d, 1H), 7.35–6.69 (m, 11H), 4.53 (t, 1H), 3.48 (m, 2H), 2.90 (m, 1H), 1.23 (d, 3H).

EXAMPLE 12

4-{2-[3,4-BIS(DIFLUOROMETHOXY)PHENYL]-2-{6-[4-(DIMETHYLSULFONYLAMINO)PHENOXY]-3-PYRIDYL}ETHYL}PYRIDINE-N-OXIDE

Step 1
4-{2-[3,4-Bis(difluoromethoxy)phenyl]-2-{6-[4-(dimethylsulfonylamino)phenoxy]-3-pyridyl}ethyl}pyridine To a 0° C. solution of 4-{2-[3,4-bis(difluoromethoxy)phenyl]-2-[6-(4-aminophenoxy)-3-pyridyl]ethyl}pyridine from Example 7, Step 1 (817 mg, 1.64 mmol) in 25 mL of $CH_2Cl_2$, was added 1.1 mL (8.2 mmol) of $Et_3N$ followed by 0.44 mL (5.74 mmol) of methylsulfonyl chloride. The resulting solution was stirred 1 h at 0° C., quenched with water and diluted with ethyl acetate. The organic layer was washed with brine, dried over $MgSO_4$ and concentrated under reduced pressure. The residue was purified by flash chromatography on silica gel (100% Ethyl acetate) to afford the disulfonamide as an amorphous solid (807 mg, 75%).

Step 2
4-{2-[3,4-Bis(difluoromethoxy)phenyl]-2-{6-[4-(dimethylsulfonylamino)phenoxy]-3-pyridyl}ethyl}pyridine-N-oxide The procedure for the oxidation of the pyridine group described in Example 1, Step 6 was applied using the product of Step 1 above as starting material. The title compound was obtained as a foam (725 mg, 88%).

$^1$H NMR (500 MHz, Acetone-$d_6$) δ 8.13 (d, 1H), 7.94 (d, 2H), 7.90 (dd, 1H), 7.50 (m, 2H), 7.42 (d, 1H), 7.34 (m, 1H), 7.28 (d, 1H), 7.20–7.16 (m, 4H), 7.00 (d, 1H), 6.96 (t, 1H), 6.93 (t, 1H), 4.57 (t, 1H), 3.49 (m, 2H), 3.48 (s, 6H).

EXAMPLE 13

4-{2-[3,4-BIS(DIFLUOROMETHOXY)PHENYL]-2-{6-[(4-HYDROXYMETHYL-3-CARBOXYL)PHENOXY]3-PYRIDYL}ETHYL}PYRIDINE-N-OXIDE SODIUM SALT

Step 1
4-{2-[3,4-Bis(difluoromethoxy)phenyl]-2-[6-(1,2-dihydro-1-isobenzofuranone-6-oxy)3-pyridyl]ethyl}pyridine-N-oxide To a solution of intermediate 3 (104 mg, 0.214 mmol) in 0.2 mL of pyridine, was added 45 mg of (0.3 mmol) of phenol followed by 45 mg of $K_2CO_3$ and 3 mg of CuO. The mixture was stirred at 170° C. for 3 h cooled down to room temperature and purified directly by flash chromatography on silica gel (10% EtOH/ethyl acetate) to afford 47 mg of the title compound.

Step 2
4-{2-[3,4-Bis(difluoromethoxy)phenyl]-2-{6-[(4-hydroxymethyl-3-carboxyl)phenoxy]3-pyridyl}methyl}pyridine-N-oxide sodium salt To a solution of lactone (23 mg, 0.041 mmol) from Step 1 above in 1 mL of ethanol, was added 0.041 mL of a 1 N solution of NaOH. The reaction was stirred 3 h at room temperature and 1 mL of water was added. The mixture was filtered and frozen dry to afford 22 mg of the title compound.

EXAMPLE 14

4-{2-[3,4-BIS(DIFLUOROMETHOXY)PHENYL]-2-[6-(BENZYLOXY)3-PYRIDYL]ETHYL}PYRIDINE-N-OXIDE

Following the procedure described in Example 1 but substituting benzyl alcohol for 4-trifluoromethoxyphenol, the title compound was obtained as a white foam (290 mg).

$^1$H NMR (500 MHz, Acetone-$d_6$) δ 8.11 (d, 1H), 7.95 (m, 2H), 7.73 (dd, 1H), 7.45–7.25 (m, 8H), 7.18 (m, 2H), 6.96 (t, 1H), 6.93 (t, 1H), 6.77 (d, 1H), 5.33 (s, 2H), 4.49 (t, 1H), 3.45 (m, 2H).

EXAMPLE 15

4-{2-[3,4-BIS(DIFLUOROMETHOXY)PHENYL]-2-[6-(1-PHENYLETHOXY)3-PYRIDYL]ETHYL}PYRIDINE-N-OXIDE

Following the procedure described in Example 1 but substituting (±)-1-phenylethanol for 4-trifluoromethoxyphenol, the title compound was obtained as a white foam (54 mg).

$^1$H NMR (500 MHz, Acetone-$d_6$) δ 8.01 (m, 1H), 7.92 (m, 2H), 7.70 (m, 1H), 7.42–7.37 (m, 3H), 7.32–7.28 (m, 3H), 7.25–7.20 (m, 2H), 7.15 (m, 2H), 6.93 (m, 2H), 6.75 (d, 1H), 6.17 (m, 1H), 4.44 (m, 1H), 3.42 (m, 2H), 1.54 (d, 3H).

EXAMPLE 16

4-{2-[3,4-BIS(DIFLUOROMETHOXY)PHENYL]-2-[6-(3,4-DIFLUOROBENZYLOXY)3-PYRIDYL]ETHYL}PYRIDINE-N-OXIDE

Following the procedure described in Example 1 but substituting 3,4-difluorobenzyl alcohol for 4-trifluoromethoxyphenol, the title compound was obtained as an oil (370 mg).

$^1$H NMR (500 MHz, Acetone-$d_6$) δ 8.12 (d, 1H), 7.96 (m, 2H), 7.77 (dd, 1H), 7.41 (m, 2H), 7.34–7.26 (m, 4H), 7.19 (m, 2H), 6.97 (t, 1H), 6.94 (t, 1H), 6.79 (d, 1H), 5.30 (m, 2H), 4.51 (t, 1H), 3.48 (m, 2H).

EXAMPLE 17

4-{2-[3,4-BIS(DIFLUOROMETHOXY)PHENYL]-2-[6-(4-METHYLSULFONYLBENZYLOXY)3-PYRIDYL]ETHYL}PYRIDINE-N-OXIDE

Step 1
2-[4-(methylthio)benzyloxy]-5-bromopyridne

To a solution of 2,5-dibromopyridine (5.0 g, 21.1 mmol) in 75.0 mL of toluene, was added 4.2 g (27.43 mmol) of 4-(methylthio)benzyl alcohol, 2.8 g (50.64 mmol) of KOH and 400 mg (0.054 mmol) of 18-crown-6. The solution was heated at refluxing temperature with a Dean-Stark apparatus for 3 h, cooled down to room temperature and rotovaped down to dryness. The residue was diluted with water/$CHCl_3$ and the organic phase was washed with brine, dried over $MgSO_4$ and concentrated under reduced pressure. The solid residue was washed with $Et_2O$/hexane and filtered to afford 3.6 g (55%) of bromide as a pale yellow solid.

Step 2
[3,4-Bis(difluoromethoxy)phenyl]-{6-[4-(methylthio)benzyloxy]-3-pyridyl}methanol To a –78° C. solution of bromopyridine from Step 1 above (1.0 g, 3.22 mmol) in 10 mL of THF, was added 1.7 mL (3.65 mmol) of a 2.1 M solution of n-BuLi. The solution was stirred 15 minutes followed by the addition of 7 mL of a THF solution of 3,4-bis(difluoromethoxy)benzaldehyde (512 mg, 2.15 mmol). The resulting solution was stirred 30 minutes at –78° C., quenched with a 25% $NH_4OAc$ solution and diluted with ethyl acetate. The organic layer was washed with brine, dried over $MgSO_4$ and concentrated under reduced pressure. The residue was purified by flash chromatography on silica gel (25% Ethyl acetate/hexane) to afford the alcohol as an oil (380 mg, 30%).

Step 3
[3,4-Bis(difluoromethoxy)phenyl]-[6-(4-methylsulfonylbenzyloxy)3-pyridyl]methanol To a solution of methyl sulfide from Step 2 above (380 mg, 0.97 mmol) in a mixture of 10 mL of $CH_2Cl_2$ and 1.0 mL of MeOH, was added MMPP (1.4 g, 2.82 mmol) in one portion. The mixture was stirred 1.5 h at room temperature, quenched with a 25% $NH_4OAc$ solution and diluted with ethyl acetate. The organic layer was washed with brine, dried over $MgSO_4$ and concentrated under reduced pressure. The residue was purified by flash chromatography on silica gel (60% Ethyl acetate/hexane) to afford the methyl sulfone as an oil (384 mg, 93%).

Step 4
[3,4-Bis(difluoromethoxy)phenyl]-[6-(4-methylsulfonylbenzyloxy)3-pyridyl]chloromethane The procedure for the formation of the chloride described in Example 1, Step 3 was applied using the product of Step 3 above as starting material. The chloride obtained was used directly for the next step without any purification.

Step 5
4-{1-Carbethoxy-2-[3,4-bis(difluoromethoxy)phenyl]-2-[6-(4-methylsulfonylbenzyloxy)-3-piridyl]ethyl}pyridine The procedure for the alkylation with ethyl 4-pyridylacetate described in Example 1, Step 4 was applied using the product of Step 4 above as starting material. The ethyl ester obtained was used directly for the next step without any purification.

Step 6
4-{2-[3,4-Bis(difluoromethoxy)phenyl]-2-[6-(4-methylsulfonylbenzyloxy)3-pyridyl]ethyl}pyridine The procedure for the hydrolysis/decarboxylation described in Example 1, Step 5 was applied using the product of Step 5 above as starting material. The pyridine was obtained as an oil (340 mg, 65% for 3 steps).

Step 7
4-{2-[3,4-Bis(difluoromethoxy)phenyl]-2-[6-(4-methylsulfonylbenzyloxy)3-pyridyl]ethyl}pyridine-N-oxide The procedure for the oxidation of the pyridine group described in Example 1, Step 6 was applied using the product of Step 6 above as starting material. The title compound was obtained as a foam (320 mg, 92%).

$^1$H NMR (500 MHz, Acetone-d$_6$) δ 8.10 (d, 1H), 7.96–7.92 (m, 4H), 7.77 (dd, 1H), 7.68 (d, 2H), 7.41 (d, 1H), 7.33 (dd, 1H), 7.27 (d, 1H), 7.18 (d, 2H), 6.97 (t, 1H), 6.94 (t, 1H), 6.84 (d, 1H), 5.46 (s, 2H), 4.50 (t, 1H), 3.46 (m, 2H), 3.12 (s, 3H).

EXAMPLE 18

(ENANTIOMER-1)-4-{2-[3,4-BIS (DIFLUOROMETHOXY)PHENYL]-2-[6-(3,5-DIFLUOROBENZYLOXY)3-PYRIDYL] ETHYL}PYRIDINE

Following the procedure described in Example 1, Step 1–5 but substituting 3,5-difluorobenzyl alcohol for 4-trifluoromethoxyphenol, the racemic title compound was obtained as a white foam. The mixture was then resolved with a preparative column: chiralpak AD, 17% i-PrOH/hexane, 70 mL/min. 650 mg of Example 18 were obtained as the fast eluting enantiomer with a retention time of 38 minutes.

$^1$H NMR (400 MHz, Acetone-d$_6$) δ 8.36 (dd, 2H), 8.10 (d, 1H), 7.78 (dd, 1H), 7.40 (s, 1H), 7.32 (dd, 1H), 7.25 (d, 1H), 7.18 (dd, 2H), 7.07 (m, 2H), 6.96 (t, 1H), 6.95 (m, 1H), 6.92 (t, 1H), 6.79 (d, 1H), 5.35 (s, 2H), 4.55 (t, 1H), 3.48 (dd, 2H).

EXAMPLE 19

(ENANTIOMER-2)-4-{2-[3,4-BIS (DIFLUOROMETHOXY)PHENYL]-2-[6-(3,5-DIFLUOROBENZYLOXY)3-PYRIDYL] ETHYL}PYRIDINE

Following the procedure described in Example 1, Step 1–5 but substituting 3,5-difluorobenzyl alcohol for 4-trifluoromethoxyphenol, the racemic title compound was obtained as a white foam. The mixture was then resolved with a preparative column: chiralpak AD, 35% i-PrOH/hexane, 75 mL/min. 640 mg of Example 19 were obtained as the slow eluting enantiomer with a retention time of 45 minutes.

$^1$H NMR (400 MHz, Acetone-d$_6$) 6 8.36 (dd, 2H), 8.10 (d, 1H), 7.78 (dd, 1H), 7.40 (s, 1H), 7.32 (dd, 1H), 7.25 (d, 1H), 7.18 (dd, 2H), 7.07 (m, 2H), 6.96 (t, 1H), 6.95 (m, 1H), 6.92 (t, 1H), 6.79 (d, 1H), 5.35 (s, 2H), 4.55 (t, 1H), 3,48 (dd, 2H).

EXAMPLE 20

(ENANTIOMER-1)-4-{2-[3,4-BIS (DIFLUOROMETHOXY)PHENYL]-2-[6-(3,5-DIFLUOROBENZYLOXY)3-PYRIDYL] ETHYL}PYRIDINE-N-OXIDE

The procedure for the oxidation of the pyridine group described in Example 1, Step 6 was applied using the product of Example 18 above as starting material. The title compound was obtained as a foam (600 mg).

$^1$H NMR (400 MHz, Acetone-d$_6$) δ 8.13 (d, 1H), 7.97 (d, 2H), 7.78 (dd, 1H), 7.41 (d, 1H), 7.34 (dd, 1H), 7.27 (d, 1H), 7.20 (d, 2H), 7.09 (dd, 2H), 6.98 (t, 1H), 6.95 (t, 1H), 6.94 (m, 1H), 6.85 (d, 1H), 5.36 (s, 2H), 4.53 (t, 1H), 3.47 (dd, 2H).

EXAMPLE 21

(ENANTIOMER-2)-4-{2-[3,4-BIS (DIFLUOROMETHOXY)PHENYL]-2-[6-(3,5-DIFLUOROBENZYLOXY)3-PYRIDYL] ETHYL}PYRIDINE-N-OXIDE

The procedure for the oxidation of the pyridine group described in Example 1, Step 6 was applied using the product of Example 19 above as starting material. The title compound was obtained as a foam (600 mg).

$^1$H NMR (400 MHz, Acetone-d$_6$) δ 8.13 (d, 1H), 7.97 (d, 2H), 7.78 (dd, 1H), 7.41 (d, 1H), 7.34 (dd, 1H), 7.27 (d, 1H), 7.20 (d, 2H), 7.09 (dd, 2H), 6.98 (t, 1H), 6.95 (t, 1H), 6.94 (m, 1H), 6.85 (d, 1H), 5.36 (s, 2H), 4.53 (t, 1H), 3.47 (dd, 2H).

EXAMPLE 22

4-{2-[3,4-BIS(DIFLUOROMETHOXY)PHENYL]-2-{6-[2-METHYL-2-(4-FLUOROPHENYL) PROPYLOXY]3-PYRIDYL}ETHYL}PYRIDINE

Step 1
2-Methyl-2-(4-fluorophenyl)propanol

To a 0° C. solution of methyl 4-fluorophenylacetate (37 mmol) in 80 mL of THF was added 83 mmol of a 1.0 M solution of NaHMDS in THF. The solution was stirred 35 miutes at 0° C. and 112 mmol od MeI were added. The reaction was stirred overnight at room temperature and quenched at 0° C. with a saturated solution of NH$_4$Cl. The aqueous layer was extracted with Et$_2$O and the combined organic layers were washed with brine, dried over MgSO$_4$ and concentrated under reduced pressure. The residue was purified by flash chromatography on silica gel (10% Et$_2$O/hexane) to afford the ester methyl-2-methyl-2-(4-fluorophenyl) propanoate. This ester (3.1 g) was then dissolved in 60 mL of THF and treated at 0° C. with 8 mL of a LiAlH$_4$ solution. The reaction was stirred 30 minutes at 0° C. and quenched with a saturated solution of NH$_4$Cl. The aqueous layer was extracted with ethyl acetate and the combined organic layers were washed with brine, dried over MgSO$_4$ and concentrated under reduced pressure. The residue was purified by flash chromatography on silica gel (40% Et$_2$O/hexane) to afford 2.7 g (100%) of alcohol.

Step 2
2-[2-methyl-2-(4-fluorophenyl)propyloxy]-5-bromopyridine

Following the procedure described in Example 17, Step 1 but substituting 2-methyl-2-(4-fluorophenyl)propanol From Step 1 above for 4-(methylthio)benzyl alcohol, the desired bromopyridine was obtained in 90% yield.

Step 3
[3,4-Bis(difluoromethoxy)phenyl]-{6-[2-methyl-2-(4-fluorophenyl)propyloxy]-3-pyridyl}methanol The coupling procedure described in Example 17, Step 2 was applied using the product of Step 2 above as starting material. The alcohol was obtained in 45% yield.

Step 4
[3,4-Bis(difluoromethoxy)phenyl]-{6-[2-methyl-2-(4-fluorophenyl)propyloxy]-3-pyridyl}chloromethane The procedure for the formation of the chloride described in Example 1, Step 3 was applied using. the product of Step 3 above as starting material. The chloride obtained was used directly for the next step without any purification.

Step 5
4-{1-Carbethoxy-2-[3,4-bis(difluoromethoxy)phenyl]-2-{6-[2-methyl-2-(4-fluorophenyl)propyloxy]-3-pyridyl}ethyl}pyridine The procedure for the alkylation with ethyl 4-pyridylacetate described in Example 1, Step 4 was applied using the product of Step 4 above as starting material. The ethyl ester obtained was used directly for the next step without any purification.

Step 6
4-{2-[3,4-Bis(difluoromethoxy)phenyl]-2-{6-[2-methyl-2-(4-fluorophenyl)propyloxy]3-pridyl}ethyl}pyridine The procedure for the hydrolysis/decarboxylation described in Example 1, Step 5 was applied using the product of Step 5 above as starting material. 641 mg of the title compound were obtained (58%, 3 Steps).

$^1$H NMR (400 MHz, Acetone-$d_6$) δ 8.36 (d, 2H), 8.06 (s, 1H), 7.69 (dd, 1H), 7.49–7.46 (m, 2H), 7.38 (s, 1H), 7.29 (q, 2H), 7.17 (d, 2H), 7.04 (t, 2H), 6.94 (t, 1H), 6.92 (t, 1H), 6.64 (d, 1H), 4.52 (t, 1H), 4.26 (s, 2H), 3.45 (d, 2H), 1.39 (s, 6H).

EXAMPLE 23

4-{2-[3,4-BIS(DIFLUOROMETHOXY)PHENYL]-2-{6-[2-METHYL-2-(4-FLUOROPHENYL) PROPYLOXY]3-PYRIDYL}ETHYL}PYRIDINE-N-OXIDE

The procedure for the oxidation of the pyridine group described in Example 3 was applied using the product of Example 22 above as starting material. The title compound was obtained as a foam (157 mg, 62%).

$^1$H NMR (400 MHz, Acetone-$d_6$) δ 8.06 (d, 1H), 7.93 (d, 2H), 7.67 (dd, 1H), 7.50–7.47 (m, 2H), 7.38 (s, 1H), 7.32 (q, 2H), 7.17 (d, 2H), 7.04 (t, 2H), 6.95 (t, 1H), 6.92 (t, 1H), 6.65 (d, 1H), 4.48 (t, 1H), 4.27 (s, 2H), 3.44 (dd, 2H), 1.40 (s, 6H).

EXAMPLE 24

4-{2-[3,4-BIS(DIFLUOROMETHOXY)PHENYL]-2-{6-[2-(4-FLUOROPHENYL)ETHOXY]3-PYRIDYL}ETHYL}PYRIDINE

Following the procedure described in Example 22, Step 2–6 but substituting 2-(4-fluorophenyl)ethanol for 2-methyl-2-(4-fluorophenyl)propanol, 820 mg of the title compound were obtained.

$^1$H NMR (400 MHz, Acetone-$d_6$) δ 8.39 (d, 2H), 8.09 (s, 1H), 7.71 (dd, 1H), 7.39 (s, 1H), 7.35 (m, 3H), 7.25 (d, 1H), 7.20 (m, 2H), 7.05 (m, 2H), 6.85 (t, 1H), 6.83 (t, 1H), 6.66 (d, 1H), 4.55 (t, 1H), 4.42 (t, 2H), 3.42 (d, 2H), 3.02 (t, 2H).

EXAMPLE 25

4-{2-[3,4-BIS(DIFLUOROMFTHOXY)PHENYL]-2-{6-[2-(4-FLUOROPHENYL)ETHOXY]3-PYRIDYL}ETHYL}PYRIDINE-N-OXIDE

The procedure for the oxidation of the pyridine group described in Example 3 was applied using the product of Example 24 above as starting material. The title compound was obtained as a foam (137 mg, 66%).

$^1$H NMR (400 MHz, Acetone-$d_6$) δ 8.08 (s, 1H), 7.93 (d, 2H), 7.70 (dd, 1H), 7.38 (s, 1H), 7.35 (m, 3H), 7.28 (d, 1H), 7.18 (d, 2H), 7.03 (t, 2H), 6.95 (t, 1H), 6.92 (t, 1H), 6.67 (d, 1H), 4.48 (t, 1H), 4.42 (t, 2H), 3.45 (dd, 2H), 3.01 (t, 2H).

EXAMPLE 26

4-{2-[3,4-BIS(DIFLUOROMETHOXY)PHENYL]-2-[6-(4-TRIFLUOROMETHYLBENZYLOXY)3-PYRIDYL]ETHYL}PYRIDINE-N-OXIDE

Following the procedure described in Example 1 but substituting 4-trifluoromethylbenzyl alcohol for 4-trifluoromethoxyphenol, 427 mg of the title compound was obtained as an oil.

$^1$H NMR (500 MHz, Acetone-$d_6$) δ 8.12 (d, 1H), 7.98 (m, 2H), 7.78 (dd, 1H), 7.70 (d, 2H), 7.65 (d, 2H), 7.43 (d, 1H), 7.33 (m, 1H), 7.28 (d, 1H), 7.20 (m, 2H), 7.00 (t, 1H), 6.96 (t, 1H), 6.83 (d, 1H), 5.43 (m, 2H), 4.52 (t, 1H), 3.47 (m, 2H).

EXAMPLE 27

4-{2-[3,4-BIS(DIFLUOROMETHOXY)PHENYL]-2-[6-(4-TRIFLUOROMETHOXYBENZYLOXY)3-PYRIDYL]ETHYL}PYRIDINE-N-OXIDE

Following the procedure described in Example 1 but substituting 4-trifluoromethoxybenzyl alcohol for 4-trifluoromethoxyphenol, 480 mg of the title compound was obtained as an oil.

$^1$H NMR (500 MHz, Acetone-$d_6$) δ 8.12 (d, 1H), 7.96 (m, 2H), 7.76 (dd, 1H), 7.57 (d, 2H), 7.41 (s, 1H), 7.32 (m, 3H), 7.27 (d, 1H), 7.19 (d, 2H), 6.98 (t, 1H), 6.94 (t, 1H), 6.79 (d, 1H), 5.36 (m, 2H), 4.51 (t, 1H), 3.46 (m, 2H).

EXAMPLE 28

4-{2-[3,4-BIS(DIFLUOROMETHOXY)PHENYL]-2-[6-(1,1-DIMETHYL-2-PHENYLETHOXY)3-PYRIDYL]ETHYL}PYRIDINE-N-OXIDE

Step 1–5
4-{2-[3,4-Bis(difluoromethoxy)phenyl]-2-[6-(1,1-dimethyl-2-phenylethoxy)3-pyridyl]ethyl}pyridine Following the procedure described in Example 22, Step 2–6 but substituting 1,1-dimethyl-2-phenylethanol for 2-methyl-2-(4-fluorophenyl)propanol the pyridine was obtained.

Step 6
4-{2-[3,4-Bis(difluoromethoxy)phenyl]-2-[6-(1,1-dimethyl-2-phenylethoxy)3-pyridyl]ethyl}pyridine-N-oxide The procedure for the oxidation of the pyridine group described in Example 3 was applied using the product of Step 5 above as starting material. The title compound was obtained as a foam (175 mg).

$^1$H NMR (400 MHz, Acetone-$d_6$) δ 8.12 (d, 1H), 7.95 (d, 2H), 7.67 (dd, 1H), 7.40 (d, 1H), 7.33 (dd, 1H), 7.26 (d, 1H), 7.12–7.23 (m, 7H), 6.96 (t, 1H), 6.92 (t, 1H), 6.60 (d, 1H), 4.47 (t, 1H), 3.46 (dd, 2H), 3.23 (d, 2H), 1.49 (s, 6H).

EXAMPLE 29

4-{2-[3,4-BIS(DIFLUORONMTHOXY)PHENYL]-2-{6-[2-THIENYLMETHOXY]3-PYRIDYL}ETHYL}PYRIDINE-N-OXIDE

Step 1–5
4-{2-[3,4-Bis(difluoromethoxy)phenyl]-2-{6-[2-thienylmethoxy]3-pyridyl}ethyl}pyridine Following the procedure described in Example 22, Step 2–6 but substituting (2-thienyl)methanol for 2-methyl-2-(4-fluorophenyl)propanol , the pyridine was obtained.

Step 6
4-{2-[3,4-Bis(difluoromethoxy)phenyl]-2-{6-[2-thienylmethoxy]3-pyridyl}ethyl}pyridine-N-oxide The procedure for the oxidation of the pyridine group described in Example 3 was applied using the product of Step 5 above as starting material. The title compound was obtained as a foam (35 mg).

$^1$H NMR (400 MHz, Acetone-$d_6$) δ 8.14 (d, 1H), 7.95 (d, 2H), 7.73 (dd, 1H), 7.43–7.41 (m, 2H), 7.31 (q, 2H), 7.20–7.15 (m, 3H), 7.00–6.97 (m, 1H), 6.97 (t, 1H), 6.94 (t, 1H), 6.72 (d, 1H), 5.50 (s, 2H), 4.51 (t, 1H), 3.52–3.42 (m, 2H).

EXAMPLE 30

4-{2-[3,4-BIS (DIFLUOROMETHOXY)PHENYL]-2-{6-[1-METHYL-1-(4-FLUOROPHENYL) ETHOXY]3-PYRIDYL}ETHYL}PYRIDINE

Following the procedure described in Example 22, Step 2–6 but substituting 1-methyl-1-(4-fluorophenyl)ethanol (Prepared by the addition of MeMgCl on 4-fluoroacetophenone) for 2-methyl-2-(4-fluorophenyl)propanol, 500 mg of the title compound were obtained.

$^1$H NMR (400 MHz, Acetone-$d_6$) δ 8.33 (d, 2H), 7.80 (d, 1H), 7.65 (dd, 1H), 7.43–7.38 (m, 2H), 7.33 (s, 1H), 7.26 (dd, 1H), 7.22 (d, 1H), 7.10 (d, 2H), 7.00 (t, 1H), 6.92 (t, 1H), 6.91 (t, 1H), 6.72 (d, 1H), 4.39 (t, 1H), 3.40 (m, 2H), 1.81 (s, 6H).

EXAMPLE 31

4-{2-[3,4-BIS(DIFLUOROMETHOXY)PHENYL]-2-{6-[1-METHYL-1-(4-FLUOROPHENYL) ETHOXY]3-PYRIDYL}ETHYL}PYRIDINE-N-OXIDE

The procedure for the oxidation of the pyridine group described in Example 3 was applied using the product of Example 30 above as starting material. The title compound was obtained as a foam (53 mg, 19%).

$^1$H NMR (400 MHz, Acetone-$d_6$) δ 7.92 (d, 2H), 7.84 (d, 1H), 7.44–7.38 (m, 2H), 7.33 (s, 1H), 7.29 (dd, 1H), 7.22 (d, 1H), 7.12 (d, 2H), 7.05 (t, 2H), 6.95 (t, 1H), 6.93 (t, 1H), 6.74 (d, 1H), 4.32 (t, 1H), 3.45–3.32 (m, 2H), 1.82 (s, 6H).

EXAMPLE 32

4-{2-[3,4-BIS(DIFLUOROMETHOXY)PHENYL]-2-[6-(4-FLUOROBENZYLOXY)3-PYRIDYL] ETHYL}PYRIDINE-N-OXIDE

Following the procedure described in Example 1 but substituting 4-fluorobenzyl alcohol for 4-trifluoromethoxyphenol, 475 mg of the title compound were obtained.

$^1$H NMR (400 MHz, Acetone-$d_6$) δ 8.11 (d, 1H), 7.94 (d, 2H), 7.74 (dd, 1H), 7.47 (dd, 2H), 7.40 (d, 1H), 7.33 (dd, 1H), 7.27 (d, 1H), 7.18 (d, 2H), 7.08–7.13 (m, 2H), 6.96 (t, 1H), 6.93 (t, 1H), 6.77 (d, 1H), 5.30 (s, 2H), 4.50 (t, 1H), 3.47 (dd, 2H).

EXAMPLE 33

4-{2-[3,4-BIS(DIFLUOROMETHOXY)PHENYL]-2-[6-(4-CHLOROBENZYLOXY)3-PYRIDYL] ETHYL}PYRIDINE-N-OXIDE

Following the procedure described in Example 1 but substituting 4-chlorobenzyl alcohol for 4-trifluoromethoxyphenol, 500 mg of the title compound were obtained.

$^1$H NMR (400 MHz, Acetone-$d_6$) δ 8.11 (d, 1H), 7.94 (d, 2H), 7.75 (dd, 1H), 7.46 (d, 2H), 7.36–7.41 (m, 3H), 7.33 (dd, 1H), 7.27 (d, 1H), 7.18 (d, 2H), 6.97 (t, 1H), 6.93 (t, 1H), 6.77 (d, 1H), 5.31 (s, 2H), 4.49 (t, 1H), 3.46 (dd, 2H).

EXAMPLE 34

4-{2-[3,4-BIS(DIFLUOROMETHOXY)PHENYL]-2-{6-[1,2-DIHYDRO-1-ISOBENZOFURANONE-6-OXY]3-PYRIDYL}ETHYL}PYRIDINE-N-OXIDE

To a solution of intermediate 3 (104 mg, 0.214 mmol) in 0.2 nm of pyridine, was added 45 mg of (0.3 mmol) of 6-hydroxyl-1,2-dihydro-1-isobenzofuranone followed by 45 mg of $K_2CO_3$ and 3 mg of CuO. The mixture was stirred at 170° C. for 3 h cooled down to room temperature and purified directly by flash chromatography on silica gel (10% EtOH/ethyl acetate) to afford 47 mg of the title compound.

$^1$H NMR (500 MHz, Acetone-$d_6$) δ 8.11 (s, 1H), 8.00–7.90 (m, 3 H), 7.69 (d, 1H), 7.55–7.47 (m, 2H), 7.44 (s, 1H), 7.34 (d, 1H), 7.28 (d, 1H), 7.20 (d, 2H), 7.03 (d, 1H), 6.97 (t, large J, 1H), 6.94 (t, large J, 1H), 5.40 (s, 2H), 4.57 (t, 1H), 3.50 (d, 2H).

PREPARATION OF INTERMEDIATES

INTERMEDIATE 1

[3,4-BIS(DIFLUOROMETHOXY)PHENYL]-(6-BROMO-3-PYRIDYL)METHANONE

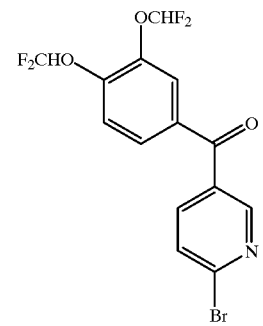

1

Step 1

[3,4-Bis(difluoromethoxy)phenyl]-(6-bromo-3-pyridyl)methanol

To a −78° C. suspension of 2,5-dibromopyridine (11.4 g, 48.0 mmol) in 300 mL of $Et_2O$, was added 40.0 mL (48.0 rmnol) of a 1.2 N solution of n-butyllithium in hexane over 10 minutes. The orange mixture was stirred (Mechanical stirrer) 10 minutes at −78° C. followed by the addition over 5 minutes of a precooled solution of bis(difluoromethoxy)benzaldehyde (9.6 g, 40.0 mmol) in 60 mL of $Et_2O$. This red solution was stirred 1 h at −78° C. and slowly poured into a saturated aqueous solution of $NH_4Cl$. The aqueous layer was extracted with ethyl acetate and the combined organic phases were washed with brine, dry over $MgSO_4$ and concentrated under reduced pressure. The residue was purified by chromatography on silica gel (Gradient 20% to 40% ethyl acetate/hexane) to afford 8.3 g (53%) of alcohol.

Step 2

[3,4-Bis(difluoromethoxy)phenyl]-(6-bromo-3-pyridyl)methanone

To a solution of alcohol (3.96 g, 10.0 mmol) from Step 1 above in 60 mL of $CH_2Cl_2$, was added 8.1 g (93.0 mmol) of $MnO_2$. The resulting mixture was stirred 20 h at room temperature and filtered on celite. the volatile were removed under reduced pressure to afford 3.48 g (88%) of ketone.

$^1$H NMR (500 MHz, Acetone-$d_6$) δ 8.72 (d, 1H), 8.10 (dd, 1H), 7.85–7.78 (m, 3H), 7.55 (d, 1H), 7.20 (t, 1H), 7.12 (t, 1H).

49

INTERMEDIATE 2

4-{2-[3,4-BIS(DIFLUOROMETHOXY)PHENYL]-
2-(6-BROMO-3-PYRIDYL)ETHYL}PYRIDNE

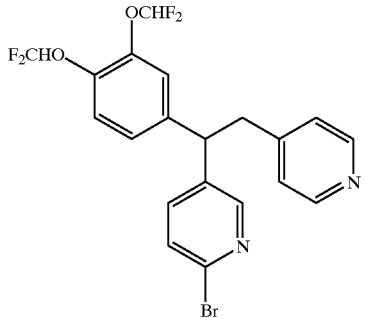

Step 1
[3,4-Bis(difluoromethoxy)phenyl]-(6-bromo-3-pyridyl) chloromethane

To a solution [3,4-Bis(difluoromethoxy)phenyl]-(6-bromo-3-pyridyl)methanol (15.8 g,40.0 mmol) in 400 mL of $CH_2Cl_2$, was added 3.8 mL (52.0 nimol) of $SOCl_2$. The solution was stirred 45 minutes at room temperature and poured into a saturated aqueous solution of $NaHCO_3$. The aqueous layer was extracted with $CH_2Cl_2$ and the combined organic layers were dry over $MgSO_4$ and concentrated under reduced pressure. The crude chloride was used directly for the next step without any purification.

Step 2
4-{1-Carbethoxy-2-[3,4-bis(difluoromethoxy)phenyl]-2-(6-bromo-3-pyridyl)ethyl}pyridine To a 0° C. solution of ethyl 4-pyridyl acetate (19.8 g, 120 mmol) in 500 mL of THF, was added 21.0 mL (120 mmol) of HMPA and 240 mL (120 mmol) of a 0.5 M solution KHMDS in toluene. The resulting mixture was stirred 15 minutes at room temperature followed by the addition over 10 minutes of a solution of the crude chloride from Step 1 above in 100 mL of THF. The reaction was stirred 1 h at room temperature, poured into a saturated aqueous solution of $NH_4Cl$ and the pH was adjusted to 7 with 1 N HCl. The aqueous layer was extracted with ethyl acetate and gthe combined organic phases were washed with brine, dry over $MgSO_4$ and concentrated under reduced pressure. The residue was used directly for the next step without any purification.

Step 3
4-{2-[3,4-Bis(difluoromethoxy)phenyl]-2-(6-bromo-3-pyridyl)ethyl}pyridine To a solution of crude ester from Step 2 above in a mixture of 540 mL of THF, 180 mL of MeOH and 180 mL of water, was added 180 mL of a 2 N solution of LiOH. The solution was stirred 1.5 h at 65° C., cooled down to room temperature and 360 mL of 1 N HCl solution were added. The mixture was rotovaped down, the residue was diluted in ethyl acetate and the organic phases was washed with brine, dry over $MgSO_4$ and concentrated under reduced pressure to afford 18.2 g (97%, 3 steps) of pure bromopyridine.

$^1$H NMR (500 MHz, Acetone-$d_6$) δ 8.40 (m, 3H), 7.78 (dd, 1H), 7.50 (d, 1H), 7.43 (s, 1H), 7.36 (dd, 1H), 7.28 (d, 1H), 7.20 (m, 2H), 6.95 (t, 1H), 6.94 (t, 1H), 4.65 (t, 1H), 3.58–3.48 (mn, 2H).

50

INTERMEDIATE 3

4-{2-[3,4-BIS(DIFLUOROMETHOXY)PHENYL]-
2-(6-BROMO-3-PYRIDYL)ETHYL}PYRIDINE

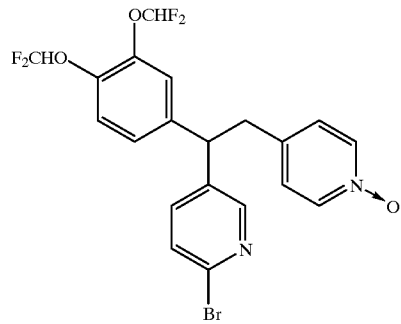

To a solution of intermediate 2 (2.0 g, 4.2 mmol) in a mixture of 30 mL of $CH_2Cl_2$ and 3 mL of MeOH was added 1.55 g (2.5 mmol) of 80% MMPP. The reaction was stirred at room temperature for 20 h and purified directly by chromatography on silica gel (Gradient 3% $Et_3N$/ethyl acetate to 30% EtOH/ethyl acetate +3% $Et_3N$ to 40% EtOH/ethyl acetate +3% $Et_3N$) to afford 1.91 g (93%) of desired pyridine-N-oxide.

$^1$H NMR (500 MHz, Acetone-$d_6$) δ 8.38 (d, 1H), 7.95 (d, 2H), 7.77 (dd, 1H), 7.51 (d, 1H), 7.41 (s, 1H), 7.35 (dd, 1H), 7.29 (d, 1H), 7.19 (d, 2H), 6.96 (t, 1H), 6.94 (t, 1H), 4.60 (t, 1H), 3.57–3.47 (m, 2H).

What is claimed is:

1. A compound represented by formula I:

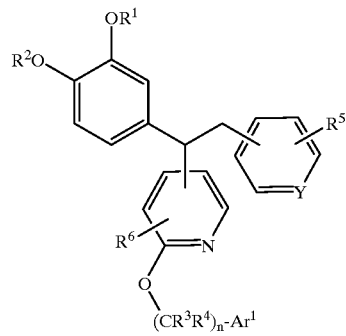

or a pharmaceutically acceptable salt or hydrate thereof wherein:

Y represents N or N-oxide;

$R^1$ and $R^2$ are independently selected from:
H, $C_{1-6}$alkyl and halo$C_{1-6}$ alkyl, $R^3$ and $R^4$ are independently selected from H and $C_{1-6}$alkyl, or $R^3$ and $R^4$ attached to the same carbon atom taken together represent a carbonyl oxygen atom, or $R^3$ and $R^4$ attached to different carbon atoms considered in combination with the carbon atoms to which they are attached along with any intervening atoms and represent a saturated 5, 6 or 7 membered carbocyclic ring, $R^5$ and $R^6$ independently represent a member selected from the group consisting of: H, $C_{1-6}$alkyl, halo$C_{1-6}$alkyl and CN;

n represents an integer of from 0–6;

Ar¹ is selected from the group consisting of:
  (a) thienyl,
  (b) thiazolyl,
  (c) pyridyl,
  (d) phenyl and
  (e) naphthyl,
said Ar¹ being optionally substituted with 1–3 members selected from the group consisting of:
  (1) halo,
  (2) $C_{1-6}$alkoxy,
  (3) $C_{1-7}$alkylthio,
  (4) CN,
  (5) $C_{1-6}$alkyl,
  (6) $C_{1-6}$hydroxyalkyl,
  (7) —$CO_2H$, —$CO_2C_{1-6}$alkyl,
  (8) $NH(SO_2Me)$, $N(SO_2Me)_2$,
  (9) $SO_2Me$,
  (10) $NO_2$,
  (11) $C_{1-6}$alkenyl,
  (12) halo $C_{1-6}$ alkyl, and
  (13) $NH_2$,
and when Ar¹ represents a phenyl or naphthyl group with two or three substituents, two such substituents may be considered in combination and represent a 5 or 6 membered fused lactone ring.

2. A compound in accordance with claim 1 wherein $R^1$ and $R^2$ are $C_{1-6}$ alkyl or halo$C_{1-6}$alkyl.

3. A compound in accordance with claim 2 wherein $R^1$ and $R^2$ are selected from the group consisting of $CH_3$, $CH_2F$, $CHF_2$ and $CF_3$.

4. A compound in accordance with claim 3 wherein $R^1$ and $R^2$ are $CHF_2$.

5. A compound in accordance with claim 1 wherein n is selected from 0, 1, 2 and 3.

6. A compound in accordance with claim 5 wherein n is selected from 0, 1 and 2.

7. A compound in accordance with claim 1 wherein $R^5$ and $R^6$ are independently selected from the group consisting of: H and $C_{1-6}$ alkyl.

8. A compound in accordance with claim 7 wherein $R^5$ and $R^6$ represent H.

9. A compound in accordance with claim 1 wherein Ar¹ is selected from phenyl and naphthyl.

10. A compound in accordance with claim 9 wherein Ar¹ is phenyl.

11. A compound in accordance with claim 1 wherein $R^3$ and $R^4$ are H or $C_{1-6}$alkyl.

12. A compound in accordance with claim 11 wherein $R^3$ and $R^4$ are H or methyl.

13. A compound in accordance with claim 1 wherein:
  $R^1$ and $R^2$ are $C_{1-6}$alkyl or halo$C_{1-6}$alkyl selected from the group consisting of $CH_3$, $CH_2F$, $CHF_2$ and $CF_3$;
  n is 0, 1, 2 or 3;
  Ar¹ is phenyl or naphthyl,
  $R^3$ and $R^4$ are H or methyl
  and $R^5$ and $R^6$ are H or $C_{1-6}$alkyl.

14. A compound in accordance with claim 13 wherein:
  $R^1$ and $R^2$ are $CHF_2$, and n is 0, 1 or 2.

15. A compound in accordance with claim 14 wherein:
  $R^1$ and $R^2$ are $CHF_2$;
  n is 0, 1 or 2;
  $R^3$ and $R^4$ are H or methyl and
  Ar¹ is phenyl.

16. A compound selected from the group consisting of:

4-{2-[3,4-Bis(difluoromethoxy)phenyl]-2-{6-[4-(trifluoromethoxy)phenoxy]3-pyridyl}ethy]}pyridine-N-oxide, 4-{2-[3,4-Bis(difluoromethoxy)phenyl]-2-[6-(4-(methoxycarbonyl)phenoxy)3-pyridyl]ethyl}pyridine, 4-{2-[3,4-Bis(difluoromethoxy)phenyl]-2-[6-(4-(methoxycarbonyl)phenoxy)3-pyridyl]ethyl}pyridine-N-oxide, 4-{2-[3,4-Bis(difluoromethoxy)phenyl]-2-{6-[4-(2-hydroxypropan-2-yl)phenoxy]3-pyridyl}ethyl}pyridine, 4-{2-[3,4-Bis(difluoromethoxy)phenyl]-2-{6-[4-(2-hydroxypropan-2-yl)phenoxy]3-pyridyl}ethyl}pyridine-N-oxide, 4-{2-[3,4-Bis(difluoromethoxy)phenyl]-2-[6-(4-nitrophenoxy)3-pyridyl]ethyl}pyridine-N-oxide, 4-{2-[3,4-Bis(difluoromethoxy)phenyl]-2-{6-[4-(methylsulfonylamino)phenoxy]3-pyridyl}ethyl}pyridine-N-oxide, 4-{2-[3,4-Bis(difluoromethoxy)phenyl]-2-{6-[4-(trifluoromethyl)phenoxy]3-pyridyl}ethyl}pyridine-N-oxide, 4-{2-[3,4-Bis(difluoromethoxy)phenyl]-2-{6-[3-(methylsulfonylamino)phenoxy]3-pyridyl}ethyl}pyridine-N-oxide, 4-{2-[3,4-Bis(difluoromethoxy)phenyl]-2-{6-[4-(2-propenyl)phenoxy]3-pyridyl}ethyl}pyridine-N-oxide, 4-{2-[3,4-Bis(difluoromethoxy)phenyl]-2-{6-[4-(2-propyl)phenoxy]3-pyridyl}ethyl}pyridine-N-oxide, 4-{2-[3,4-Bis(difluoromethoxy)phenyl]-2-{6-[4-(dimethylsulfonylamino)phenoxy]3-pyridyl}ethyl}pyridine-N-oxide, 4-{2-[3,4-Bis(difluoromethoxy)phenyl]-2-{6-[(4-hydroxymethyl-3-carboxyl)phenoxy]3-pyridyl}ethyl}pyridine-N-oxide sodium salt, 4-{2-[3,4-Bis(difluoromethoxy)phenyl]-2-[6-(benzyloxy)3-pyridyl]ethyl}pyridine-N-oxide, 4-{2-[3,4-Bis(difluoromethoxy)phenyl]-2-[6-(1-phenylethoxy)3-pyridyl]ethyl}pyridine-N-oxide, 4-{2-[3,4-Bis(difluoromethoxy)phenyl]-2-[6-(3,4-difluorobenzyloxy)3-pyridyl]ethyl}pyridine-N-oxide, 4-{2-[3,4-Bis(difluoromethoxy)phenyl]-2-[6-(4-methylsulfonylbenzyloxy)3-pyridyl]ethyl}pyridine-N-oxide, (Enantiomer-1)-4-{2-[3,4-Bis(difluoromethoxy)phenyl]-2-[6-(3,5-difluorobenzyloxy)3-pyridyl]ethyl}pyridine, (Enantiomer-2)-4-{2-[3,4-Bis(difluoromethoxy)phenyl]-2-[6-(3,5-difluorobenzyloxy)3-pyridyl]ethyl}pyridine, (Enantiomer-1)-4-{2-[3,4-Bis(difluoromethoxy)phenyl]-2-[6-(3,5-difluorobenzyloxy)3-pyridyl]ethyl}pyridine-N-oxide, (Enantiomer-2)-4-{2-[3,4-Bis(difluoromethoxy)phenyl]-2-[6-(3,5-difluorobenzyloxy)3-pyridyl]ethyl}pyridine-N-oxide, 4-{2-[3,4-Bis(difluoromethoxy)phenyl]-2-{6-[2-methyl-2-(4-fluorophenyl)propyloxy]3-pyridyl}ethyl}pyridine, 4-{2-[3,4-Bis(difluoromethoxy)phenyl]-2-{6-[2-methyl-2-(4-fluorophenyl)propyloxy]3-pyridyl}ethyl}pyridine-N-oxide, 4-{2-[3,4-Bis(difluoromethoxy)phenyl]-2-{6-[2-(4-fluorophenyl)ethoxy]3-pyridyl}ethyl}pyridine, 4-{2-[3,4-Bis(difluoromethoxy)phenyl]-2-{6-[2-(4-fluorophenyl)ethoxy]3-pyridyl}ethyl}pyridine-N-oxide,
4-{2-[3,4-Bis(difluoromethoxy)phenyl]-{2-[6-(4-trifluoromethylbenzyloxy]3-pyridyl}ethyl}pyridine-N-oxide,
4-{2-[3,4-Bis(difluoromethoxy)phenyl]-2-[6-(4-trifluoromethoxybenzyloxy)3-pyridyl]ethyl }pyridine-N-oxide,
4-{2-[3,4-Bis(difluoromethoxy)phenyl]-2-[6-(1,1-dimethyl-2-phenylethoxy)3-pyridyl]ethyl}pyridine-N-oxide,
4-{2-[3,4-Bis(difluoromethoxy)phenyl]-2-[6-(2-thienylmethoxy)3-pyridyl]ethyl}pyridine-N-oxide,
4-{2-[3,4-Bis(difluoromethoxy)phenyl]-2-{6-[1-methyl-1-(4-fluorophenyl)ethoxy]3-pyridyl}ethyl}pyridine,
4-{2-[3,4-Bis(difluoromethoxy)phenyl]-2-{6-[1-methyl-1-(4-fluorophenyl)ethoxy]3-pyridyl}ethyl}pyridine-N-oxide,
4-{2-[3,4-Bis(difluoromethoxy)phenyl]-2-[6-(4-fluorobenzyloxy)3-pyridyl]ethyl}pyridine-N-oxide,
4-{2-[3,4-Bis(difluoromethoxy)phenyl]-2-[6-(4-chlorobenzyloxy)3-pyridyl]ethyl}pyridine-N-oxide,
4-{2-[3,4-Bis(difluoromethoxy)phenyl]-2-{6-[1,2-dihydro-1-isobenzofuranone-6-oxy]3-pyridyl}ethyl}pyridine-N-oxide or a pharmaceutically acceptable salt or hydrate thereof.

17. A compound in accordance with claim 1 selected from one of the following tables:

TABLE 2

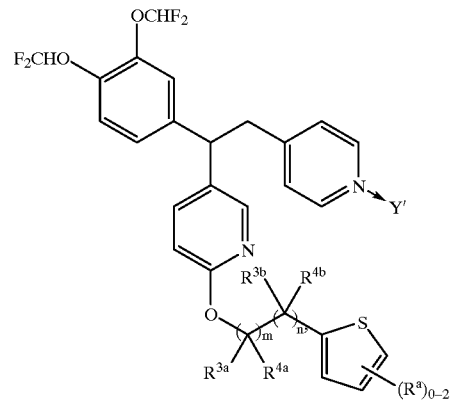

| Y' | m | $R^{3a}$ | $R^{4a}$ | n' | $R^{3b}$ | $R^{4b}$ | $R^a$ |
|---|---|---|---|---|---|---|---|
| O | 0 | — | — | 0 | — | — | 4-(trifluoromethoxy) |
| — | 0 | — | — | 0 | — | — | 4-(methoxycarbonyl) |
| O | 0 | — | — | 0 | — | — | 4-(methoxycarbonyl) |
| — | 0 | — | — | 0 | — | — | 4-(2-hydroxypropan-2-yl) |
| O | 0 | — | — | 0 | — | — | 4-(2-hydroxypropan-2-yl) |
| O | 0 | — | — | 0 | — | — | 4-nitro |
| O | 0 | — | — | 0 | — | — | 4-(methylsulphonyl amino) |
| O | 0 | — | — | 0 | — | — | 4-(trifluoromethyl) |
| O | 0 | — | — | 0 | — | — | 5-(methylsulphonyl amino) |
| O | 0 | — | — | 0 | — | — | 4-(2-propenyl) |
| O | 0 | — | — | 0 | — | — | 4-(2-propyl) |
| O | 0 | — | — | 0 | — | — | 4-(dimethylsulphonyl amino) |
| O | 0 | — | — | 0 | — | — | 4-(hydroxymethyl)-5-(carboxyl) |
| O | 1 | H | H | 0 | — | — | — |

TABLE 2-continued

| Y' | m | $R^{3a}$ | $R^{4a}$ | n' | $R^{3b}$ | $R^{4b}$ | $R^a$ |
|---|---|---|---|---|---|---|---|
| O | 1 | Me | H | 0 | — | — | — |
| O | 1 | H | H | 0 | — | — | 4,5-difluoro |
| O | 1 | H | H | 0 | — | — | 4-(methylsulfonyl) |
| — | 1 | H | H | 0 | — | — | 3-fluoro |
| — | 1 | H | H | 0 | — | — | 4,5-difluoro |
| O | 1 | H | H | 0 | — | — | 4,5-dichloro |
| O | 1 | H | H | 0 | — | — | 5-fluoro |
| — | 1 | H | H | 1 | Me | Me | 4-fluoro |
| O | 1 | H | H | 1 | Me | Me | 4-fluoro |
| — | 1 | H | H | 1 | H | H | 5-fluoro |
| O | 1 | H | H | 1 | H | H | 4-fluoro |
| O | 1 | H | H | 0 | — | — | 4-(trifluoromethyl) |
| O | 1 | H | H | 0 | — | — | 4-(trifluoromethoxy) |
| O | 1 | Me | Me | 1 | H | H | — |
| O | 1 | Me | H | 0 | — | — | — |
| — | 1 | Me | Me | 0 | — | — | 4-fluoro |
| O | 1 | Me | Me | 0 | — | — | 4-fluoro |
| O | 1 | H | H | 0 | — | — | 4-fluoro |
| O | 1 | H | H | 0 | — | — | 4-chloro |

TABLE 3

| Y' | m | $R^{3a}$ | $R^{4a}$ | n' | $R^{3b}$ | $R^{4b}$ | $R^a$ |
|---|---|---|---|---|---|---|---|
| O | 0 | — | — | 0 | — | — | 4-(trifluoromethoxy) |
| — | 0 | — | — | 0 | — | — | 4-(methoxycarbonyl) |
| O | 0 | — | — | 0 | — | — | 4-(methoxycarbonyl) |
| — | 0 | — | — | 0 | — | — | 4-(2-hydroxypropan-2-yl) |
| O | 0 | — | — | 0 | — | — | 4-(2-hydroxypropan-2-yl) |
| O | 0 | — | — | 0 | — | — | 4-nitro |
| O | 0 | — | — | 0 | — | — | 4-(methylsulphonyl amino) |

TABLE 3-continued

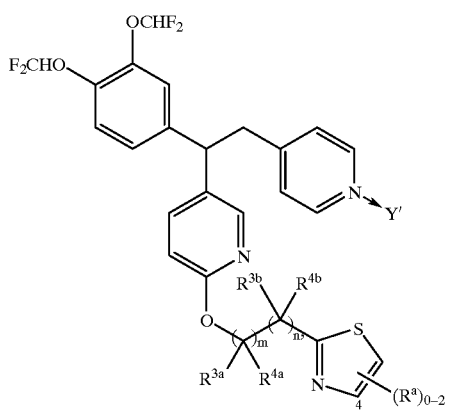

| Y' | m | R³ᵃ | R⁴ᵃ | n' | R³ᵇ | R⁴ᵇ | Rᵃ |
|---|---|---|---|---|---|---|---|
| O | 0 | — | — | 0 | — | — | 4-(trifluoromethyl) |
| O | 0 | — | — | 0 | — | — | 5-(methylsulphonyl amino) |
| O | 0 | — | — | 0 | — | — | 4-(2-propenyl) |
| O | 0 | — | — | 0 | — | — | 4-(2-propyl) |
| O | 0 | — | — | 0 | — | — | 4-(dimethylsulphonyl amino) |
| — | 0 | — | — | 0 | — | — | 4-(hydroxymethyl)-5-(carboxyl) |
| O | 1 | H | H | 0 | — | — | — |
| O | 1 | Me | H | 0 | — | — | — |
| O | 1 | H | H | 0 | — | — | 4,5-difluoro |
| O | 1 | H | H | 0 | — | — | 4-(methylsulfonyl) |
| — | 1 | H | H | 0 | — | — | 4,5-dichloro |
| — | 1 | H | H | 0 | — | — | 5-fluoro |
| O | 1 | H | H | 0 | — | — | 4,5-dichloro |
| O | 1 | H | H | 0 | — | — | 5-fluoro |
| — | 1 | H | H | 1 | Me | Me | 4-fluoro |
| O | 1 | H | H | 1 | Me | Me | 4-fluoro |
| — | 1 | H | H | 1 | H | H | 4-fluoro |
| O | 1 | H | H | 1 | H | H | 4-fluoro |
| O | 1 | H | H | 0 | — | — | 4-(trifluoromethyl) |
| O | 1 | H | H | 0 | — | — | 4-(trifluoromethoxy) |
| O | 1 | Me | Me | 1 | H | H | — |
| O | 1 | H | H | 0 | — | — | — |
| O | 1 | Me | Me | 0 | — | — | 4-fluoro |
| O | 1 | Me | Me | 0 | — | — | 4-fluoro |
| O | 1 | H | H | 0 | — | — | 4-fluoro |
| O | 1 | H | H | 0 | — | — | 4-chloro |

TABLE 4

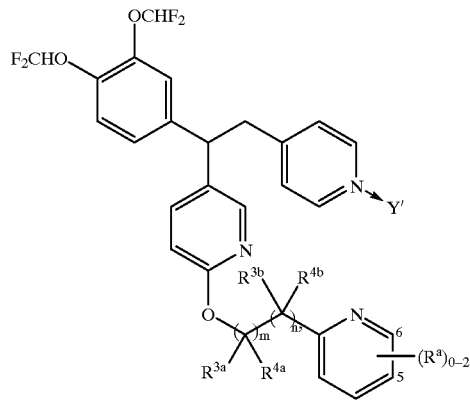

| Y' | m | R³ᵃ | R⁴ᵃ | n' | R³ᵇ | R⁴ᵇ | Rᵃ |
|---|---|---|---|---|---|---|---|
| O | 0 | — | — | 0 | — | — | 6-(trifluoromethoxy) |
| — | 0 | — | — | 0 | — | — | 6-(methoxycarbonyl) |
| O | 0 | — | — | 0 | — | — | 6-(methoxycarbonyl) |
| — | 0 | — | — | 0 | — | — | 6-(2-hydroxypropan-2-yl) |
| O | 0 | — | — | 0 | — | — | 6-(2-hydroxypropan-2-yl) |
| O | 0 | — | — | 0 | — | — | 6-nitro |
| O | 0 | — | — | 0 | — | — | 6-(methylsulphonyl amino) |
| O | 0 | — | — | 0 | — | — | 6-(trifluoromethyl) |
| O | 0 | — | — | 0 | — | — | 5-(methylsulphonyl amino) |
| O | 0 | — | — | 0 | — | — | 6-(2-propenyl) |
| O | 0 | — | — | 0 | — | — | 6-(2-propyl) |
| O | 0 | — | — | 0 | — | — | 6-(dimethylsulphonyl amino) |
| O | 0 | — | — | 0 | — | — | 5-(hydroxymethyl)-6-(carboxyl) |
| O | 1 | H | H | 0 | — | — | — |
| O | 1 | Me | H | 0 | — | — | — |
| O | 1 | H | H | 0 | — | — | 5,6-difluoro |
| O | 1 | H | H | 0 | — | — | 6-(methylsulfonyl) |
| — | 1 | H | H | 0 | — | — | 4,6-difluoro |
| — | 1 | H | H | 0 | — | — | 5,6-dichloro |
| O | 1 | H | H | 0 | — | — | 4,6-difluoro |
| O | 1 | H | H | 0 | — | — | 5,6-dimethyl |
| — | 1 | H | H | 1 | Me | Me | 6-fluoro |
| O | 1 | H | H | 1 | Me | Me | 6-fluoro |
| — | 1 | H | H | 1 | H | H | 6-fluoro |
| O | 1 | H | H | 1 | H | H | 6-fluoro |
| O | 1 | H | H | 0 | — | — | 6-(trifluoromethyl) |
| O | 1 | H | H | 0 | — | — | 6-(trifluoromethoxy) |
| O | 1 | Me | Me | 1 | H | H | — |
| O | 1 | H | H | 0 | — | — | — |
| — | 1 | Me | Me | 0 | — | — | 6-fluoro |
| O | 1 | Me | Me | 0 | — | — | 6-fluoro |
| O | 1 | H | H | 0 | — | — | 6-fluoro |
| O | 1 | H | H | 0 | — | — | 6-fluoro |

TABLE 5

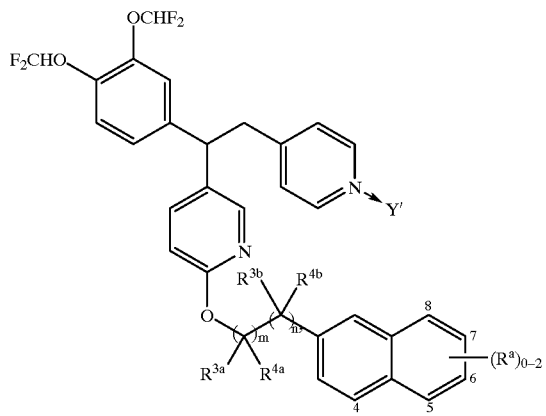

| Y' | m | R³ᵃ | R⁴ᵃ | n' | R³ᵇ | R⁴ᵇ | Rᵃ |
|---|---|---|---|---|---|---|---|
| O | 0 | — | — | 0 | — | — | 7-(trifluoromethoxy) |
| — | 0 | — | — | 0 | — | — | 7-(methoxycarbonyl) |
| O | 0 | — | — | 0 | — | — | 7-(methoxycarbonyl) |
| — | 0 | — | — | 0 | — | — | 7-(2-hydroxypropan-2-yl) |
| O | 0 | — | — | 0 | — | — | 7-(2-hydroxypropan-2-yl) |
| O | 0 | — | — | 0 | — | — | 7-nitro |
| O | 0 | — | — | 0 | — | — | 7-(methylsulphonyl amino) |
| O | 0 | — | — | 0 | — | — | 7-(trifluoromethyl) |
| O | 0 | — | — | 0 | — | — | 6-(methylsulphonyl amino) |
| O | 0 | — | — | 0 | — | — | 7-(2-propenyl) |
| O | 0 | — | — | 0 | — | — | 7-(2-propyl) |
| O | 0 | — | — | 0 | — | — | 7-(dimethylsulphonyl amino) |
| O | 0 | — | — | 0 | — | — | 6-(hydroxymethyl)-7-(carboxyl) |
| O | 1 | H | H | 0 | — | — | — |
| O | 1 | Me | H | 0 | — | — | — |
| O | 1 | H | H | 0 | — | — | 6,7-difluoro |
| O | 1 | H | H | 0 | — | — | 7-(methylsulfonyl) |
| — | 1 | H | H | 0 | — | — | 6,7-difluoro |
| — | 1 | H | H | 0 | — | — | 5,7-difluoro |
| O | 1 | H | H | 0 | — | — | 5-fluoro |
| O | 1 | H | H | 0 | — | — | 6-fluoro |
| — | 1 | H | H | 1 | Me | Me | 7-fluoro |
| O | 1 | H | H | 1 | Me | Me | 7-fluoro |
| — | 1 | H | H | 1 | H | H | 7-fluoro |
| O | 1 | H | H | 1 | H | H | 7-fluoro |
| O | 1 | H | H | 0 | — | — | 7-(trifluoromethyl) |
| O | 1 | H | H | 0 | — | — | 7-(trifluoromethoxy) |
| O | 1 | Me | Me | 1 | H | H | — |

TABLE 5-continued

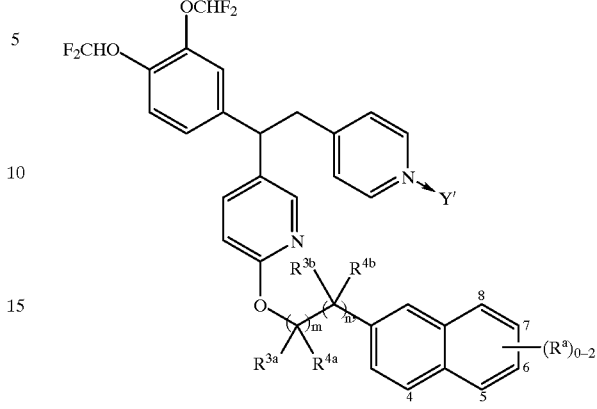

| Y' | m | R³ᵃ | R⁴ᵃ | n' | R³ᵇ | R⁴ᵇ | Rᵃ |
|---|---|---|---|---|---|---|---|
| O | 1 | H | H | 0 | — | — | — |
| — | 1 | Me | Me | 0 | — | — | 7-fluoro |
| O | 1 | Me | Me | 0 | — | — | 7-fluoro |
| O | 1 | H | H | 0 | — | — | 7-fluoro |
| O | 1 | H | H | 0 | — | — | 7-chloro |

18. A pharmaceutical composition that is comprised of a compound in accordance with claim 1 in combination with a pharmaceutically acceptable carrier.

19. A method of treating or preventing a disease or condition mediated by PDE 4, comprising administering to a mammalian patient in need thereof, a compound in accordance with claim 1 in an amount that is effective to treat or prevent said disease or condition.

20. A method in accordance with claim 19 wherein the disease or condition is slected from the group consisting of: asthma, inflammed lung associated with asthma, cystic fibrosis, inflammatory airway disease, chronic bronchitis, eosinophilic granuloma, psoriasis, other benign and malignant proliferative skin diseases, endotoxic shock, septic shock, ulcerative colitis, Crohn's disease, reperfusion injury of the myocardium or brain, inflammatory arthritis, chronic glomerulonephritis, atopic dermatitis, urticaria, adult respiratory distress syndrome, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, tumour growth and cancerous invasion of normal tissues.

21. A method of treating or preventing asthma in a mammalian patient in need of such treatment or prevention, comprising administering to said patient a compound in accordance with claim 1 in an amount that is effective for treating or preventing asthma.

* * * * *